United States Patent
Smith

(10) Patent No.: US 7,517,644 B1
(45) Date of Patent: Apr. 14, 2009

(54) METHOD AND COMPOSITIONS FOR CELLULAR REPROGRAMMING

(75) Inventor: Larry J. Smith, 1019 S. 106th Plz., Apartment # 104, Omaha, NE (US) 68114

(73) Assignee: Larry J. Smith, Omaha, NE (US)

( * ) Notice: Subject to any disclaimer, the term of this patent is extended or adjusted under 35 U.S.C. 154(b) by 0 days.

(21) Appl. No.: 08/472,801

(22) Filed: Jun. 7, 1995

Related U.S. Application Data

(63) Continuation-in-part of application No. 08/426,781, filed on Apr. 22, 1995, now abandoned, which is a continuation-in-part of application No. 07/748,997, filed on Aug. 23, 1991, now abandoned.

(51) Int. Cl.
*C07H 21/02* (2006.01)
*A61K 31/70* (2006.01)
*C12Q 1/68* (2006.01)

(52) U.S. Cl. .................. 435/6; 435/375; 435/377; 514/44; 536/23.1; 536/24.1; 536/24.5

(58) Field of Classification Search .................. 435/6; 536/24.1, 24.5; 514/44
See application file for complete search history.

(56) References Cited

OTHER PUBLICATIONS

Yuen et al, Clinical Studies of Antisense Therapy in Cancer, Jun. 2001, Frontiers in Bioscience, d588-593.*
Hawkins et al, Sys. Admin. of a Phosphorothioate Oligonucleotide with a Sequence Complementary to p53 for Acute Myelogenous Leukemia and Myelodysplastic Syndrome: Initial Results of a Phase I Trial, 1993, Antisense Research and Devel., vol. 3, pp. 383-390.*
Bishop et al, Phase I Trial of an Antisense Oligonucleotide OL(1)p53 in Hematologic Malignancies, Apr. 1996, Journal of Clinical Oncology, vol. 14, No. 4, pp. 1320-1326.*
CM Barton et al, Antisense Oligonucleotides directed against p53 have antiproliferative effects unrelated to effects on p53 expression, 1995, British Journal of Cancer, vol. 71, pp. 429-437.*
Sudhir Agrawal, Antisense Oligonucleotides: towards clinical trials, Oct. 1996, Tibtech, vol. 14, pp. 376-387.*

* cited by examiner

*Primary Examiner*—Sean McGarry
(74) *Attorney, Agent, or Firm*—Dann, Dorfman, Herrell & Skillman; Kathleen D. Rigaut

(57) ABSTRACT

The present invention provides methods and compositions useful in treating certain diseases herein termed "Aberrant Programming Diseases," including cancer and AIDS. According to one aspect of the invention, there is provided a method for treating an individual having an Aberrant Programming disease comprising administering to said individual an effective amount of a composition selected from the group consisting of an expression vector, a double stranded oligodeoxynucleotide, and an antisense oligodeoxynucleotide; said composition capable of regulating expression of a transcriptional regulator, said transcriptional regulator being expressed by the Aberrant Programming cells and further characterized by exhibiting a therapeutically useful change in said cell behavior in the Reprogramming Test. In a separate embodiment new antisense oligodeoxynucleotides are provided.

17 Claims, 3 Drawing Sheets

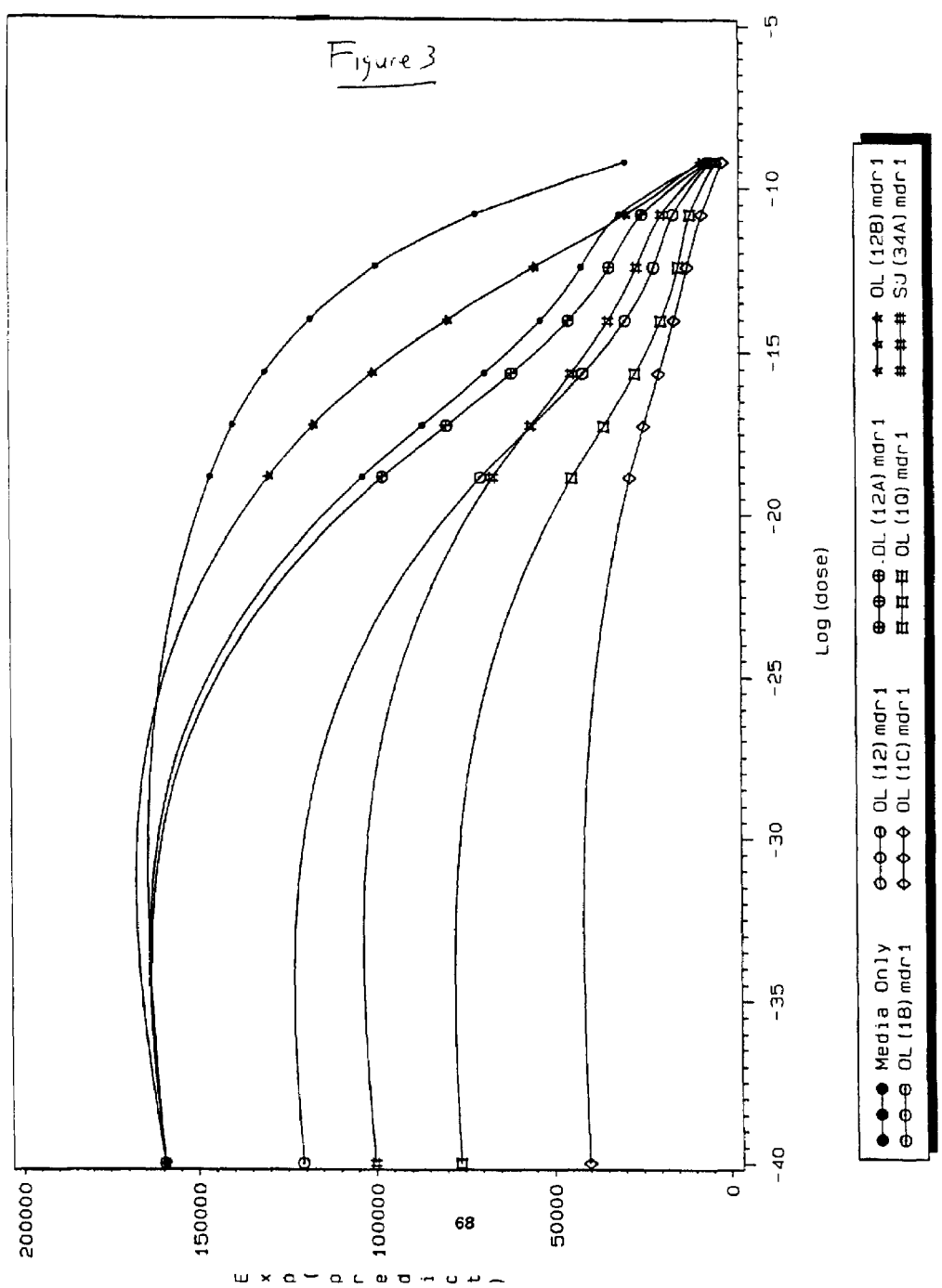

METHOD AND COMPOSITIONS FOR CELLULAR REPROGRAMMING

This is a Continuation-in-Part of application Ser. No. 08/426,781, filed 22 Apr. 1995, now abandoned which itself was filed as a Continuation-in-Part of application Ser. No. 07/748,997, filed 23 Aug. 1991 now abandoned.

BACKGROUND OF THE INVENTION

1. Field of the Invention

The present invention relates to methods and compositions useful in treating disorders in which the direct cause of the clinical disorder is the expression in the primary diseased cells of a differentiation program that does not normally exist. Such disorders are hereinafter referred to as Aberrant Programming (AP) Diseases. The invention also relates to method and compositions useful in therapeutically reprogramming normal cells.

As will be discussed more fully hereinafter, the AP diseases of this invention constitute a new disease classification and there is presented a novel molecular model of pathogenesis for these diseases. According to the molecular model of this invention, the basic disease causing entity in the AP diseases is a specific type of relational alteration among certain cellular components involved in program control. It is unlike any previously described molecular pathogenic mechanism. This model defines the nature of the therapy for these diseases, limits the potential set of therapeutically useful targets to a relatively small number of genes and leads to the unobvious conclusion that this includes the manipulation of certain "normal" genes is an appropriate approach for the treatment of AP diseases, thus, leading to a unique approach to therapy for the AP diseases of this invention. This model makes the selection of targets for proposed therapy straightforward and accessible to anyone skilled in the art. Also provided herein is a novel approach to diagnosing and developing prognostic criteria for the Aberrant Programming Diseases.

A preferred embodiment relates to the reprogramming of cell behavior through the manipulation of transcriptional regulators (TRs). The invention includes systemic treatment and compositions for such treatment, as well as in vitro manipulation of cells prior to transplantation of such cells with the host under treatment.

As will be discussed more fully hereinafter, a method is also disclosed for selecting target sites in the RNA transcripts of particular genes that individually have a high likelihood of being excellent target sites for the binding of antisense oligonucleotides which are intended to inhibit the expression of the corresponding gene. In a preferred embodiment, this target site selection method can be used to select antisense oligonucleotides for the treatment of Aberrant-Programming Diseases in accordance with the molecular model of Aberrant Programming Diseases disclosed herein. Taken together, this molecular model of Aberrant Programming Diseases (AP Model), which delimits the preferred gene targets for the development of the new therapies discussed herein for said diseases, and the method for selecting target sites within the transcripts of said genes, greatly simplifies the drug discovery process for the development of new treatment modalities and greatly increases the likelihood that clinically successful compounds will, thereby, be generated.

In yet another embodiment, the novel method disclosed herein for selecting antisense oligonucleotide target sites (and, thereby, the sequence of the corresponding antisense oligonucleotides) can be used with conventional rationale (independent of the AP model) by one with ordinary skill in the art to select therapeutic oligonucleotides for the treatment of a variety of diseases and medical purposes. The conventional rationale is, in essence, a rationale which links the known function(s) of particular molecules, in terms of their direct effects on specific cellular functions, with particular disease processes or therapeutic needs (as opposed to molecules such as TR that—non-obviously—may act indirectly as a result of being part of a combinatorial regulation mechanism).

2. Description of the Related Art

Very recent studies involving the use of antisense oligonucleotides for treatment of cancer have been reviewed by Stein and Cohen, Cancer Res. 48:2659 (1988). Several types of antisense molecules have been screened for their ability to inhibit the synthesis of particular proteins using both intact cells and in vitro systems for protein synthesis (See Ld. and Paoletti, Anti-Cancer Drug Design 2:325, 1988). For example, agents with specificity for RNA transcribed from the myc gene have been reported to inhibit the proliferation of the human AML line HL60 (Wickstrom, et al., Proc. Natl. Acad. Sci. USA 85:1028 (1988) and normal T lymphocytes (Heikkila, et al., Nature 328:445 (1987), and oligodeoxynucleotides complementary to cyclin mRNA have been reported to suppress the division of 3T3 cells (Jaskulski, et al. 1988).

More recently, it has been found that in the treatment of cancer with ODNs against myb, the proliferation of leukemic cells was inhibited with an accompanying lower degree of inhibition against normal cells. (Calabretta et al, PNAS, 88, 2351,1991.) Also, it has been shown that transient inhibition in a leukemia cell line resulted with an ODN against myc; however, unfortunately, a comparable inhibition against normal cells occurred (Zon et al patent). This patent also discloses inhibition of HIV replication using ODNs targeted to viral genes. Belenska et al (Science, 250, 997, 1990) have proposed the use of double stranded ODNs, binding to TR ligands as potential therapeutic agents for disease causing genes. They give blocking of NF-kB binding to HIV enhancer as an example. The use of retroviral vectors carrying antisense oncogenes for the treatment of cancer is known.

The fundamental problem with the foregoing part is that it is based on the notion that the expression of specific molecular abnormalities (altered regulation or mutation of endogenous genes or expression of exogenous genes) in the disease cells of these patients directly cause the clinical pathological features of the AP disease. It follows from such thinking that the therapeutic strategies should be directed to attacking these molecular abnormalities.

In the case of cancer, contemplated therapy involving antisense expression vector ODNs have been directed to oncogenes in accordance with the oncogene/anti-oncogene cancer model, or to growth factors expressed by cancer cells in accordance with the autocrine model. In the case of AIDS therapeutic strategies involving such agents being developed are directed toward blocking HIV expression and/or infection. There are no counterpart causal agents identified to the other AP diseases. Hence the therapeutic approaches under development are more empirical.

The present inventor first described in detail, in writing, in a confidential manuscript prepared for Gerald Zon, Ph.D. of Applied Biosystems Incorporated (now LYNX Therapeutics, Inc.) and completed in May of 1990, the concept of Aberrant Programming disease and the derivative notion of using antisense ODNs to modulate TR as a means of selectively reprogramming the cellular programs of the diseases cells/tissue in question. According to the AP disease model the fundamental pathology causing the clinical pathological features of these disorders is both relational and dynamic. In stark contrast to the prior art, the therapy of the present invention involves manipulation of patterns of TR expression. The invention provides an entirely new approach to the treatment of said selected diseases and provides a rational, empirical basis for the design of novel agents. The therapeutic reprogramming of normal tissue involving ODNs is unprecedented.

The Aberrant Programming model indicates that atherosclerosis is, for example, an Aberrant Programming Disease. In this case, atherosclerosis is said to result from a change in the pattern of expression of certain TR in the smooth muscle cells (SMC) associated with blood vessels; the changed pattern of expression of TR, then, is responsible for the particular differentiated state that characterizes atherosclerotic SMC and which, therefore, produces the disease. The conventional hypothesis that attempts to provide a molecular explanation for the pathogenic changes in atherosclerotic smooth muscle cells (SMC) is called the "monoclonal hypothesis" (Benditt and Benditt, Proc. Natl. Acad. Sci. USA 70: 1753, 1973). In essence, this hypothesis argues that atherosclerotic plaques are benign tumors that result from a mutagenic event in some key regulatory molecule, in a manner analogous to the conversion of a proto-oncogene to an oncogene in the case of malignant tumor cell development. In support of this "monoclonal hypothesis" it has been found that DNA isolated from cells recovered from atherosclerotic plaques is capable of transforming normal fibroblasts in a transfection-nude mouse assay, whereas DNA extracted from normal control endothelial cells does not induce such transformation. The gene(s) which are responsible for encoding this transforming capacity have not been identified, however. Ruled out so far are N-ras, K-ras, Ha-ras, erbA, erbB, fes, src, mos, Abl, sis, c-fos, c-myb and c-myc which have been shown to be expressed by SMC (Parkes et al., Am. J. Pathol. 138: 765, 1991). Thus, the "monoclonal hypothesis" requires the mutation of some key regulatory molecule as the causal factor in the development of atherosclerosis. It follows from the conventional rationale that this key regulatory molecule which is altered is the prime target for therapeutic intervention.

In contrast, the Aberrant Programming model argues that the basic molecular pathology in the atherosclerotic SMC is to be found in the pattern of TR expression, where the relevant TR are those involved in cellular program control. The Aberrant Programming model, therefore, identifies TR such as, for example, c-fos, c-myb and c-myc as being appropriate targets for evaluating potential therapeutic antisense ODNs for atherosclerosis in the Reprogramming Test (as defined hereinafter), even though these TR have not been found to be mutated in atherosclerotic SMC. If the molecular mutations that have been detected in the transfection-nude mouse assay contribute to the pathogenesis of atherosclerosis, they would be considered by the AP model to be "risk factors". Risk factors in this context are defined as determinants that increase the probability that the afflicted cells/tissue will express an altered pattern of TR, thereby facilitating the generation of an Aberrant differentiation program. The AP model sets the foundation for a novel therapeutic strategy. The model predicts, for example, that there are antisense ODNs which, when targeted to certain TR, will produce a therapeutic reprogramming of atherosclerotic SMC (such as, for example, reversing the Aberrant cellular differentiation program to a more normal state, or, inducing apoptosis in the atherosclerotic SMC); the AP model also predicts that such effects will not be seen when the antisense ODN is used to treat a wide variety of other normal and diseased cell types that express different differentiation programs, even though they express the same TR target and the expression of said TR may be down regulated by the antisense ODN treatment. The basis of this logic can best be understood by making an analogy to "language", as is done in Table I.

Rosenberg and his colleagues, using a rat model system, explored the potential use 30 of c-myb antisense ODNs for the treatment of restenosis. Restenosis refers to the re-occlusion of atherosclerotic blood vessels following a medical procedure to reverse the obstruction to blood flow produced by atherosclerotic plaques (Simons and Rosenberg, Circulation Res 70: 835, 1992; and, Simons et al., Nature 359: 67, 1992) (United States Patent Application #723454, 28 Jun. 1991; United States Patent Application #792146, 08 Nov. 1991; United States Patent Application #855416, 18 Mar. 1992). The second of the published studies demonstrates that the local delivery of phosphorothioate ODNs to rat carotid arterial SMC in vivo results in a substantial uptake of the ODNs by the SMC and a prolonged retention of these compounds by the SMC. These investigators showed that c-myb antisense ODN, but not the corresponding sense ODN, inhibited the proliferation of SMC in the aorta of normal animals following regional damage to the vessel wall resulting from balloon angioplasty. Balloon angioplasty damages the endothelium underlying the region of treatment and causes intimal migration and proliferation of the SMC over the length of the damaged blood vessel. The result of treating the damaged vessels with the c-myb antisense ODN was a substantial improvement in the patency of the affected vessel after the induced trauma, compared to control animals not treated with the c-myb antisense ODN. The c-myb antisense ODN used to treat the normal smooth muscle cells either in vitro or in vivo, however, had four guanine bases in a row which could cause the formation of a "G-quartet", while the control ODN did not. The suppression of SMC growth, therefore, may not have been due to an antisense effect on c-myb, but rather from a non-antisense effect, with the reduction in c-myb expression in the SMC being a secondary event. This possibility was not apparently explored by these investigators.

Three groups have examined the possibility that c-myc antisense ODNs might be useful for the treatment of restenosis. Zalewski and his colleagues were the first to carry out these studies (Shi et al., Circulation 88: 1190, 1992; and Shi et al., Circulation 90: 944, 1994) (United States Patent Application #4799, published 7 Jan. 1993). The first of the Zalewski papers examined the usefulness of c-myc antisense ODNs for inhibiting the proliferation of normal human SMC. The c-myc antisense ODN was shown to inhibit the proliferation of the SMC while the corresponding sense ODN and a mismatched control ODN did not. The published in vivo work by Shi et al. (1994) again demonstrated that phosphorothioate ODNs can be readily delivered to SMC in the coronary vessels of animals where the ODNs are taken up in sufficient quantities to produce biological effects. Specifically, coronary blood vessels of pigs were damaged by balloon angioplasty. The human c-myc antisense ODN or the corresponding sense control ODN, were then applied to the damaged vessels. It was not reported, however, whether or not the human c-myc antisense ODN was sufficiently complementary to the c-myc transcript of the pig to permit effective binding of the human ODN sequence to the pig target transcripts. The c-myc, but not the control ODN, substantially inhibited the proliferation of SMC, resulting in improved blood flow through the affected vessels, compared to control animals not treated with the c-myc antisense ODN. Again, however, the antisense ODN used in the in vivo efficacy studies had four guanine bases in a row, while the control ODN did not. This four-guanine sequence could explain the capacity of the "therapeutic" ODN to inhibit the proliferation of the pig SMC and to inhibit the c-myc expression, while the "control" ODN did not. Bennett et al. (J. Clin. Invest. 93: 820, 1994) and Biro et al. (Proc. Natl. Acad. Sci. USA 90: 654, 1993), using the same c-myc antisense ODNs and control ODNS, demonstrated an inhibition of rat SMC proliferation in vitro.

Hence, the published studies of the use of c-myb or c-myc antisense ODNs to block experimentally-induced restenosis in animal models could be interpreted as showing that proliferation of cells (in this case, normal smooth muscle cells) can be blocked simply by exposure to compounds which have a non-specific capacity to inhibit proliferation (such as, for example, by non-specific masking of cell surface receptors, or by interference in essential metabolic pathways). Hence, these findings do not constitute "cellular reprogramming" for the purposes of achieving a therapeutic effect as defined herein. A "true reprogramming event" that involves inhibition of proliferation in accordance with the rationale provided herein would show a dependence on the differentiation status of the target cells; i.e., the reprogramming event (initiated by the antisense ODNs) must only work on cells that exhibit a particular set of differentiation programs, and not work on cells which exhibit a different set of differentiation programs. For example, an antisense ODN capable of blocking SMC proliferation by a reprogramming effect would not be able to block the proliferation of human cells in general. The possibility remains, however, that antisense ODNs directed to c-myc or c-myb could cause a therapeutic reprogramming of atherosclerotic SMC, in accordance with the present invention. This possibility remains because the appropriate experiments have not yet been done.

The design of antisense oligonucleotides for the inhibition of gene expression has been based primarily on one or the other (or both) of two considerations. First, investigators have targeted antisense oligonucleotides to regions of RNA transcripts known to be involved in the control of pre-mRNA processing or mRNA translation, such as splice sites or the start codon (AUG), respectively. Second, investigators have used computer models of the secondary structure of mRNA to "visualize" mRNA regions that might be susceptible to ODN targeting; these structural modeling procedures are not, however, highly predictive of the actual secondary structure of the mRNA in situ. Design of antisense ODNs according to novel methods disclosed in the present invention, however, is not dependent on either of these approaches to antisense ODN design. Rather, disclosed. herein is a novel computer-based method for selecting unique "hotspots" in RNA transcripts that are particularly well suited for targeting antisense oligonucleotides for the purpose of inhibiting the expression of genes and thereby greatly enhancing the likelihood of producing therapeutic effects. The method herein described appears to be an unexpected and substantial improvement over the two conventional approaches to selecting target sites for antisense oligonucleotides.

There are now many examples of the successful use of antisense ODNs to selectively block the expression of any of a wide variety of gene targets, both in in vivo and in in vitro studies. For example, in in vivo model systems: inhibition of Human Immunodeficiency Virus (HIV) gene expression (including tax gene) in human cells grown as xenogeneic transplants in animal models (Kitajima et al., J. Biol. Chem. 267: 25881, 1992);targeting genes in xenotransplanted human cancer cells in animal models, including targeting c-myc, c-Ha-ras, NF-KB, c-myb, c-kit and bcr-Abl (Agrawal et al., Proc. Natl. Acad. Sci. USA 86: 7790, 1989; Agrawal et al., Proc. Natl. Acad. Sci. USA 88: 7595, 1991; Biro et al., Proc. Natl. Acad. Sci. USA 90: 654, 1993; Gray et al., Cancer Res. 53: 577, 1993; Higgins et al., Proc. Natl. Acad. Sci. 90: 9901, 1993; Ratajczak et al., Proc. Natl. Acad. Sci. USA 89: 11823, 1992; Wickstrom et al., Cancer Res. 52: 6741, 1992; Skorski et al., Proc. Natl. Acad. Sci. USA 91: 4504, 1994). In each of these instances involving the administration of antisense ODNs to treat animals with xenogeneic human cancers, the transplanted malignant cells were found to regress.

A number of difficulties, however, have also been reported in the use of antisense ODNs in in vitro studies, none of which have proven to be insurmountable, however, in view of the existing art and technology. In general, problems in the in vitro use of antisense ODNs (most commonly phosphorothioates) have centered around what has been viewed as "poor uptake" and/or the production of unintended biologic effects; i.e., non-antisense effects. These unintended effects fall into two major categories: first, there are biologic effects that are attributable to the backbone structure of the oligonucleotides; and, second, there are sequence-specific non-antisense (aptameric) effects that appear to be dependent upon the three-dimensional conformation of the ODN in solution, and, consequently, on the positioning of the molecular electrostatic (ionic) charges associated with the ODN molecule. Like ODN antisense effects, both of these non-antisense effects are dose dependent.

There are large differences in the capacity of similar ODNs directed to transcripts of a given gene to block the expression of that gene in cells; the reasons appear to be related to variations in the availability of the particular target site on the transcript complementary to the antisense ODN. No method has previously been described which permits antisense ODNs to be designed so that, with a high probability, some will exhibit optimal activity in the purpose intended. Hence, what has been referred to as the "poor uptake" of ODNs by some cell types in vitro may in large part reflect the use of antisense ODNs that are not properly designed and are, therefore, not optimally potent. It is also possible that the culturing of cell lines under atmospheric oxygen conditions (which is the usual and common in vitro practice) produces a situation in which antisense ODNs are made less active than they may be at much reduced (and more physiologically-relevant) oxygen tensions (Smith L J and Kay H D. Unpublished observations). The basis of this latter phenomenon could be due, at least in part, to the increased generation of reactive free oxygen radicals under ambient (atmospheric) oxygen levels by cells following treatment with any of several types of ODNs, such as phosphorothioates. Highly-reactive free oxygen radicals have been shown to have the capacity to alter the lipids in the surface membranes of cells, and to activate certain second-messenger pathways. Such alterations could lead to an inhibition of antisense ODN uptake and/or to other non-antisense ODN-dependent biologic effects.

A complete blockade of the induction of free radical formation by cells in response to exposure to ODNs at physiologic oxygen levels would require the presence of potent anti-oxidants such as, for example, vitamin C or vitamin E. Finally, in general, it appears that antisense ODNs are more active when used on freshly-obtained patient specimens than they are when used on established cell lines, either in vitro or in vivo. Furthermore, at least some established cell lines appear to be more responsive to antisense ODNs when studied in vivo in animal models than when studied in vitro in cell cultures. Dean and McKay (Proc Natl Acad Sci USA 91: 11762, 1994), for example, found that an antisense ODN directed to $PKC_a$ could inhibit the growth of the C127 murine mammary epithelial cell line both in vitro and in vivo. To get enough ODN into the cells grown in vitro to reduce $PKC_a$ expression and inhibit growth, cationic liposomes had to be utilized. The naked antisense ODN, however, worked very well when injected into mice carrying the C127 cell line as a transplant. Again, this greatly-superior in vivo response is consistent with the concept that the ODNs cause a much lower level of free radical production in the animal.

Similarly, the apparent unintended backbone-dependent biologic effects of antisense phosphorothioate ODNs on treated cells can be eliminated (or adequately reduced) by the use of more appropriately designed (and, therefore, more efficacious) antisense ODNs. These unintended biologic effects, of which the inhibition of cell proliferation is most common, generally only occur at phosphorothioate concentrations of 5-10 micromolar ($\mu M$) or greater in the final culture medium. The better designed and more potent antisense ODNs, however, are biologically most active at least 10-fold lower concentrations, particularly when fresh tissue is used, or when the antisense ODN is used in vivo.

Pronounced aptameric effects usually appear to be the property of only a small proportion of ODN. Aptameric effects result when an ODN binds tightly and specifically to a particular biomolecule, and, as a result, modifies the biological function/behavior of said biomolecule. Aptameric effects are dependent on the nucleotide sequence in the ODN. Presumably, the sequence dependence of these effects reflects the fact that ODNs with different nucleotide sequences assume different spacial conformations, dictated by neighboring nucleotide-nucleotide interactions. The nature of the backbone chemistry, however, is also relevant in aptameric effects since said chemistry (and associated molecular electrostatic [ionic] charges) also influences the overall spacial conformation which the ODN molecule can assume in solution. Only a subset of the possible aptameric effects which an ODN might produce, however, would be expected to be an absolute counter-indication for therapeutic use as an antisense compound. Any such undesirable effects can be overcome by simply choosing another antisense ODN directed to the same target transcript, but which contains a different nucleotide base sequence, or, in some instances, by changing the ODN backbone. The former option may involve selecting an entirely different "hotspot" on the transcript, or simply making modest changes (length, position) in the ODN in question. Changes in ODN secondary structure may also be achieved by making a small number of base substitutions, such as with inosine, that do not interfere significantly with binding of the ODN to the target RNA transcript.

In contrast, some antisense ODNs may possess aptameric-like effects that enhance their therapeutic efficacy. The present inventor, for example, has found that some antisense ODNs (in particular, phosphorothioate ODNs) which target MDR1 gene transcripts (and thereby inhibit P-glycoprotein expression) apparently can also reduce MDR1 mRNA levels by an aptameric-like effect that presumably involves the inhibition of second messenger pathways such as the protein kinase-C and/or protein kinase A pathways.

Many of the in vitro successes in the application of antisense ODNs for therapeutic purposes have been readily extrapolated to in vivo use. This is evidenced by the numerous publications showing the in vivo efficacy of antisense ODNs. Furthermore, several ODNs have already been approved by the United States Food and Drug Administration for clinical testing. It should be noted that the ODN uptake problems sometimes encountered in in vitro studies have not been reported to be problematic in in vivo studies. Pharmacologic/toxicologic studies of phosphorothioate antisense ODNs have shown that phosphorothioates are adequately stable under in vivo conditions, and that they are readily taken up by all the tissues in the body following systemic administration (Iversen P I, Anticancer Drug Design 6:531, 1991; Antisense Res Develop 4:43, 1994; Crooke, Ann Rev Pharm Toxicol 32: 329,1992; Cornish et al., Pharmacol Comm 3: 239,1993; Agrawal et al., Proc Natl Acad Sci USA 88: 7595, 1991; Cossum et al., J. Pharm. Exp. Therapeutics 269: 89, 1994). In addition, these compounds readily gain access to the tissue in the central nervous system following injection into the cerebral spinal fluid (Osen-Sand et al., Nature 364: 445,1993; Suzuki et al., Amer J. Physiol. 266: R1418,1994; Draguno et al., Neuroreport 5: 305, 1993; Sommer et al., Neuroreport 5: 277, 1993; Heilig et al., Eur. J. Pharm. 236: 339, 1993; Chiasson et al., Eur J. Pharm. 227: 451, 1992). Phosphorothioates per se have been found to be relatively non-toxic, although a few particular ODNs have produced unintended toxic effects in animals. The latter instances of toxicity seem to be attributable to an unexpected aptameric effect on the part of the ODN in question.

In summary, it appears that antisense ODNs have the essential properties which make them useful as therapeutic agents, both in vivo and in vitro. In vitro antisense activities now can reasonably be expected to be seen in vivo. Two major areas needed for further development of antisense ODNs as therapeutic agents involve (a) the choice of gene targets for diseases like cancer and atherosclerosis, Alzheimer's and schizophrenia, and (b) methods for the selection of optimally active antisense ODNs directed to a particular gene target. These needs are addressed by the novel inventions herein described in the present invention.

SUMMARY OF THE INVENTION

In accordance with this invention, there is provided a method for reprogramming cell behavior to achieve therapeutic effects through manipulating patterns of TR expression. Also provided is a method for treating an individual having an AP disease comprising administering to said individual an effective amount of a composition selected from the group consisting of an expression vector, a double stranded ODN, and an antisense ODN. Said composition must be capable of regulating expression of a TR. Said TR is expressed by the AP cells and further characterized by the fact that it exhibits a therapeutically useful change in said cell behavior in the Reprogramming Test of this invention (hereinafter more fully described). It is noted that when the AP disease is AIDS, said TR is not encoded by HIV. In the case of cancer, said TR is a Traitor Gene of this invention (more fully discussed hereinafter) and, preferably, excludes oncogenes, e.g. fos, myc, myb, rel, jun (in an altered form).

Another embodiment of this invention is a method for treating an individual having a clinical disorder comprising administering to said individual an effective amount of a composition selected from the group consisting of a double stranded ODN and an antisense ODN. The composition is capable of regulating expression of a TR. The TR is expressed by therapeutically relevant cells and is further characterized by exhibition of a therapeutically useful change in said cell behavior in the Reprogramming Test of this invention.

The invention revealed here primarily embodies a new type of therapy based on reprogramming cellular behavior. Collateral inventions, however, also follow including: (1) the diagnosis and/or staging of aberrant programming diseases by assaying for the expression of particular transcriptional regulators and their variants in diseased cells; and, (2) for any given aberrant program disease, the use of test agents in vitro for determining the optimum agent(s) for treating any particular patient.

Thus, there is provided a method for diagnosing or staging an AP disease comprising identifying the relevant subset of TRs expressed by AP cells from an AP patient. A method for selecting the most efficacious treatment regimen for an AP disease forms another embodiment. This embodiment comprises identifying the relevant subset of TRs expressed by AP cells from an AP patient. These embodiments are described more fully hereinafter.

In addition, the invention provides a method for treating therapeutically relevant cells from an individual having a clinical disorder prior to transplantation of the cells back into the individual (autologous transplant) embodiment. This embodiment comprises the steps of:

a) obtaining therapeutically relevant cells from the individual and b) exposing the therapeutically relevant cells to a reprogramming amount of an ODN having a sequence complementary to a sequence of RNA transcribed from a TR regulated gene or double stranded ODN ligand of a transcriptional regulator present in the TR cells. In a preferred embodiment the cells are taken from prenatal tissue or from a different donor than the individual under treatment (allogeneic transplant).

Selection of the most efficacious treatment regimen for an AP disease forms another embodiment of this invention. This method involves removing and culturing AP disease cells from an AP disease patient with an antisense ODN specific to a TR from the relevant subset of TRs expressed by AP cells from an AP patient or a double stranded ODN to the DNA binding domain of such TR to determine optimal treatment.

In carrying out the methods of treating AP diseases of this invention it is critical to select the proper targets. Hence, an important embodiment of this invention is a method for the selection of a target for the treatment of an AP disease comprising (i) determining the subset of transcriptional regulators and their direct modifiers expressed by the aberrantly programmed tissue, the corresponding normal tissue, or the constitutively self-renewing normal tissue or, alternatively, making a similar determination for any other normal tissue that is to be therapeutically manipulated in accordance with this invention; (ii) adding or subtracting expression of transcriptional regulator(s), or their direct modifiers, from cells to be therapeutically reprogrammed and the appropriate control tissue; (iii) scoring effect on cellular programming and selecting potential therapeutic agents according to the Reprogramming Test; (iv) testing effect of addition or subtraction of the function of particular transcriptional regulators, using the agents selected, (in an animal model system if the therapeutic agents are for systemic use), and (v) reducing or eliminating any undesirable side effects that might be produced by the potential therapeutic agents. This embodiment is described in detail hereinafter.

Exploiting specific cell type differences in target RNA for selecting differentially available sites for ODN binding forms another embodiment of this invention. This embodiment comprises a method for cell type dependant targeting of specific RNA transcripts comprising selecting an ODN capable of binding to and leading to the destruction of said RNA in the tissue to be therapeutically manipulated, but not in tissue where side effects are produced by destruction of said RNA. Exemplary is the use of an antisense ODN directed to cyclooxygenase RNA that selectively binds to and destroys said RNA in hematopoietic tissue while avoiding said RNA in gastrointestinal tissue.

All of the foregoing embodiments involve reprogramming of cell behavior to achieve therapeutic effects through manipulating patterns of TR expression.

Yet another embodiment of this invention is a novel computer-based method for selecting "hotspots" in the transcripts of particular genes, which hotspots define the possible sequences that the corresponding antisense ODNs can take. These hotspots include the binding sites for the most highly active of the possible antisense ODNs as judged by their capacity to suppress the expression of the corresponding gene. This computer method, based on the commercially-available "OLIGO" program created by Dr. Wojciech Rychlik (Rychlik and Rhoads, Nucleic Acids Res. 17: 8543, 1989; copyrighted 1989) utilizes parameters intuitively chosen by the inventor to direct the "OLIGO" computer program in the selection of antisense ODNs that have a high probability of being highly active. In this novel approach, the two criteria conventionally used to select antisense ODNs (RNA secondary structure and biologically functional domains within RNA transcripts) are ignored. The criteria for ODN selection used in the novel method described herein relate to the base-sequence-dictated physical properties of the prototype or test antisense ODNs, the nucleotide base sequence of which is determined by the nucleotide sequence of the "hotspot" region of a particular gene being evaluated.

When applied to the analysis of transcripts of TRs or their direct modifiers, this novel computer-based method can be used to select the most highly active therapeutic antisense ODNs for the treatment of Aberrant Programming Diseases in accordance with the Aberrant Programming Disease model disclosed herein, or for the therapeutic reprogramming of normal cellular functions. In addition, antisense ODNs designed by the novel computer-based method disclosed can be used to block the expression of genes known to be directly implicated in a variety of disease processes or which are known to be directly involved in biologic functions of therapeutic importance. ("Direct" involvement of a particular molecule in this context is to be contrasted with the direct involvement of patterns of expression of particular regulatory molecules [as part of a combinatorial regulation system that controls the cellular differentiation program and subprograms such as proliferation and apoptosis], as considered by the Aberrant Programming model in cellular reprogramming). These direct cause-and-effect associations between particular molecules or groups of molecules and particular disease or other biologic processes make the choice of possible target gene for therapeutic antisense ODN inhibition obvious to one with ordinary skill in the art. As examples: (1) β-amyloid precursor and apolipoprotein E are implicated in the pathogenesis of Alzheimer's Disease. They are, therefore, obvious antisense targets, as are (2) vascular endothelial growth factor (VEGF) which is implicated in cancer and in Rheumatoid Arthritis; (3) cyclooxygenase which is involved in pathologic inflammatory conditions such as Arthritis; and (4) the expression of molecules known to be directly involved in the regulation of apoptosis, such as the variants of bax, bcl-2, and bcl-x, which can be blocked by antisense ODNs for the purposes of promoting or inhibiting apoptosis in accordance with the therapeutic needs of the situation. It would be desirable to block apoptosis, for example, following ischemic damage resulting from the occlusion of blood vessels leading to an organ such as the heart or brain. Conversely, it would be desirable to Dromote apoptosis in malignant or atherosclerotic-programmed cells. Associations between particular target genes and disease processes are shown in Table X.

Table XI lists some of the gene/proteins other than transcriptional regulators that have been implicated in the control of apoptosis or programmed cell death. Select antisense ODNs directed to these targets should be therapeutically useful for the treatment of the diseases/conditions listed in Table XII, which lists some of the diseases/processes in which apoptosis (or programmed cell death) appears to play a key role.

The antisense ODNs targeted to TR or their direct modulators selected by the criteria disclosed herein can find uses beyond the treatment of the Aberrant Programming Diseases in accordance with the Aberrant Programming model. For example:

(1) TR involved in the control of cellular programming also can function to control the expression of particular genes such as telomerase and β-amyloid precursor protein which are implicated in the production of certain disease processes (Sp-1, Ap-1 and Ap-4, for example, are among the TR known to regulate β-amyloid precursor protein expression; and certain Hox genes are likely to be involved in the control of telomerase expression). Hence, blocking the expression of TR required for the expression of these medically important molecules can find therapeutic use. Other TR not involved in the regulation of cellular programs are restricted in their function to controlling the expression of particular genes associated with a particular state of cellular differentiation, or controlling the expression of housekeeping genes. These latter genes can be of clinical importance, and antisense ODNs which inhibit expression of TR involved in promoting or controlling the disease process may produce a desirable therapeutic effect. Examples of such TR include Ref-1, and, possibly, members of the GADD family of TR.

(2) TR encoded by the host cell are known to be important for the expression and functioning of infecting viruses. Indeed, blocking the action of NF-Kβ in HIV-infected cells by ODNs have been shown to reduce HIV expression. Examples of virally-induced diseases that would benefit from such treatment include, but are not to be limited to, those caused by HIV, HTLV, CMV, Herpes simplex, measles viruses, the hepatitis virus variants, rhinoviruses, influenza viruses and hemorrhagic fever viruses. Host-encoded transcriptional regulators that are known to regulate the following types of virus are given as examples:

HIV: USF, Elf-1, Ap-1, Ap-2, Ap-4, Sp-1, Sp-3, Sp-4, p53, NF-kβ, rel, GATA-3, UBP-1, EBP-P;

CMV: SRF, NF-kβ, p53, Ap-1, IE-2, C/EBP;

Herpesviruses: USF, Spi-1, Spi-B, ATF, CREB and C/EBP families, E2F, YY-1, Oct-1, Ap-1, Ap-2, c-myb, NF-kβ;

Hepatitis viruses: NF-1, Ap-1, Sp-1, RFX-1, RFX-2, RFX-3, NF-kβ, Ap-2, C/EBP.

(3) Arguably, TR—particularly those involved in the control of cellular programming—also regulate higher-order functioning in the nervous system. Antisense ODNs directed to c-fos, for example, have been shown to alter neurological functioning in animal models (Dragunow et al., Neuroreport. 5: 305, 1993). According to the present invention, altered patterns of TR expression in nerve cells can result in Aberrant Programming of the nerve cells, resulting in certain mental disorders such as schizophrenia. Hence, antisense ODNs, selected using the method described herein are expected to be of use for such diverse medical needs as the treatment of psychoses, depression and epilepsy.

Table X provides a general overview of some of the diseases in which the gene targets presented herein have been implicated. All of the transcriptional regulators (and their direct modifiers) known to be involved in the regulation of cellular differentiation, proliferation and/or apoptosis cellular programs (or "Programmed Cell-Death") are candidates for the preferred embodiment which is the treatment of Aberrant Programming Diseases in accordance with the Aberrant Programming model. Particular subsets of these TR that are appropriate targets for developing antisense therapeutics for a particular disease are delimited by determining which of these TR are expressed by the diseased cells in question.

Hotspots and prototype ODNs are also provided for certain transcriptional regulators that have not yet been implicated in the control of these cellular programs. This association, or lack thereof, can be established by anyone with ordinary skill in the art, using established methods. The appropriate disease applications of antisense ODNs directed to the other gene targets for which "hotspots" and prototype antisense ODNs have been provided herein are related on the usual cause-and-effect basis discussed elsewhere herein.

It follows from the AP model that there is not simply just one possible "therapeutic solution" when one is confronted with developing an antisense ODN therapeutic to treat 30 AP diseases in accordance with the present invention. That is, several different antisense ODNs—directed against different members of a select set of TR gene targets—may be active in treating the same disease. This situation is a direct consequence of the facts that (a) the TR involved in cellular programming are acting in an interdependent way as part of a combinatorial regulation system, and that (b) different TR combinations can direct the same change in cellular programming. In the analogy given between the AP cellular programming model and the grammatical rules of the English language (see Table I), the latter phenomenon is referred to as "synonyms".

Thus, as a consequence of the nature of the AP diseases and as a consequence of the nature of the non-antisense ODN effects on cells, it will not be possible a priori to determine on purely theoretical grounds which particular antisense ODNs will be useful for the treatment of any given AP disease. The major advantage of the present invention over the prior art is that it makes the fundamental nature of the AP diseases comprehensible, and, thereby, allows the most rational approach possible to be applied to the treatment of these diseases. This rational approach which is laid out here is an enormous improvement over the prior art in that—in combination with the methods described herein for selecting antisense ODNs—it makes it possible to have a rapid advance in the development of therapy for diseases that have been almost totally intractable using the existing art.

FIG. 3 is a graph showing the effects of different MDR oligonucleotides on thymine incorporation into 8226/Dox4 cells.

DESCRIPTION OF THE PREFERRED EMBODIMENTS

AP Disease Model and List

Figure 1:
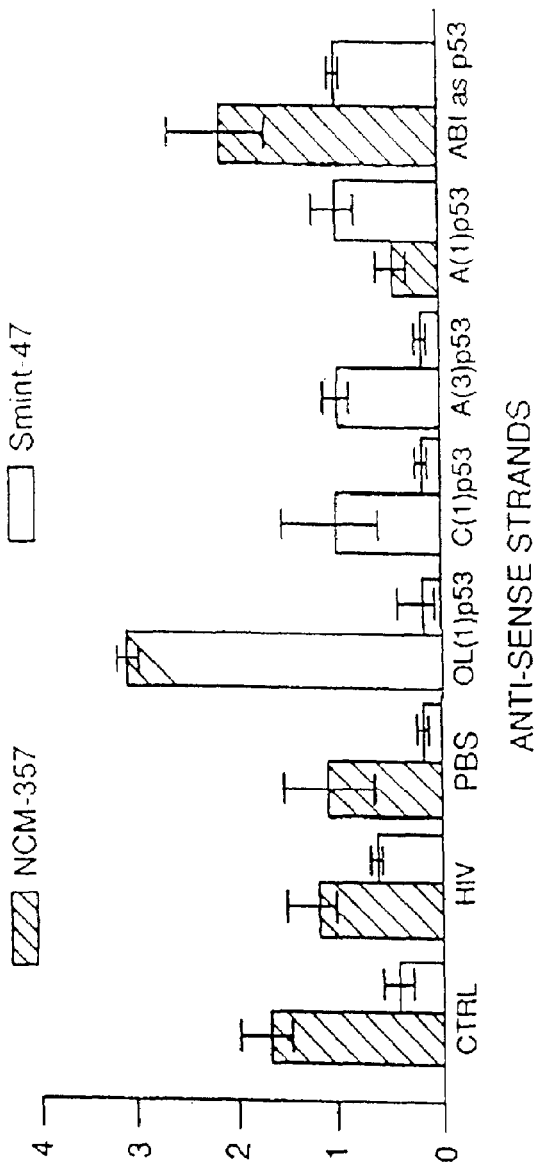
FIG. 1 is a graph showing the effects of antisense oligonucleotides on incorporation of thymidine into DNA in G1 cells.

Definition of a "cellular program"
The coordinated appearance in cells of a cell type restricted pattern of gene expression over time that provides for a particular phenotype and as a result for the determination of the range of possible cellular responses to exogenous stimuli.

The fundamental program can be thought of as a differentiation program which in turn controls the subprogram responses of the cell to environmental and other exogenous cues where the subprograms include cellular viability (apoptosis) and proliferation.

Definition of an "Aberrant Programming Disease"

One in which the direct cause of the clinical disorder is the expression in the primary diseased cells of a differentiation program that does not normally exist. That is, there is an expression of normal genes that provide for particular differentiated phenotype in abnormal combinations. The result is that these diseased cells become capable of expressing pathogenic behaviors involving cellular differentiation, viability and proliferation. These attributes of the primary diseased cells can also induce pathologic change, in their tissue environment.

The term "direct cause" with respect to pathogenesis is to be distinguished from "risk factors." Typically an AP Disease will be associated with numerous risk factors that in various combinations appear to "cause" the appearance of the disease. In fact, however, they cause the changes in the pattern of transcription regulator (TR) expression and chromatin domain availability which in turn causes the disease. This is important because programs can evolve and can become independent of any risk factors involved in their induction. Risk factors include mutagenic events, viruses, chromosomal abnormalities, genetic inheritance, and diet.

Aberrant programming disorders can be manifested as either a hyperplastic or a hypoplastic (degenerative) disease or a combination of both.

Examples of diseases where the aberrant program phenotype is expressed:
Cancer
Myeloproliferative Diseases
polycythemia vera
agnogenic myeloid metaplasia
essential thrombocytosis
Myelodysplasias
refractory anemia
refractory anemia with ringed sideroblasts
refractory anemia with excess blasts
refractory anemia with excess blasts in transition
Atherosclerosis
AIDS-related complex
AIDS
Alzheimer's Disease
Autoimmune Diseases, including:
inflammatory bowel diseases
multiple sclerosis
Rheumatoid arthritis
Systemic lupus erythematosus
Schizophrenia Molecular Model According to the molecular model set forth herein, the basic disease causing entity in the AP diseases is a specific type of relational alteration among certain cellular components involved in program control. It is unlike any previously described molecular pathogenic mechanism. This model defines the nature of a novel therapy for these diseases, limits the potential set of therapeutically useful targets to a relatively small number of genes and leads to the unobvious conclusion that the manipulation of certain "normal" genes is an appropriate approach for the treatment of AP diseases, in this way the model makes the reduction to practice of the proposed therapy straightforward and accessible to anyone skilled in the art.

Specifically, the essential molecular pathology in the AP diseases consists of changes in the interdependent patterns of TR expression and/or chromatin domain availability for transcription. In turn, these relational alterations provide for the expression of abnormal cellular programs involving cellular differentiation which are pathogenic. Particular TR or certain molecules involved with the control of domain status may be structurally abnormal. However, these are not necessarily useful targets for therapeutic intervention.

Tenets of the model relevant to the development of specific therapy:

A) Those true of both normal and aberrant programming:
1) The pattern of domain availability determines the possible range of genes that can be expressed in the cell and, therefore, limits the range of cellular programs that can be expressed.
2) The pattern of TR expression is the molecular equivalent of a programming code. By analogy with language particular combinations of TR (letters) working as a unit (words) regulate the expression of sets of genes in a coordinate fashion while the complete set of TR combinations used in any given cell (sentence) determines which of the possible phenotypes the cell will expressed, and therefore the overall character of the cell's differentiation program (see Table I for more details where cancer is used as an example).
3) Only a subset of the total number of TRs involved in the control of cellular differentiation for the total organism are expressed in any given cell type and they are few in number.
4) Similar effects on particular patterns of gene expression (programming) can be achieved by more than one specific combination of TR (synonyms).
5) The specific functional consequences of a particular TR's being expressed is context-dependent. That is, its effects on cellular programming depends both on which other TR it combines to regulate a particular set of genes (what words it appears in) and on the total set of different TR combination expressed by the cell (the sentence).

B) True of AP cells but not normal cells:
1) The combinations of TR seen in AP cells is different from that seen in any normal cell (the sentence is not expressed by any normal cell).
2) The specific functional consequences of any given particular TR being expressed in an AP cell, therefore, will be different from the consequences seen in a normal cell.
3) AP cells, therefore, express a cellular differentiation program that is different from any normal differentiation program. As a result AP cells express pathogenic behaviors resulting from their altered differentiation, viability and proliferation characteristics.
4) Hence, equivalent manipulations of the expression of a given TR in normal cells vs. aberrantly programmed cells can produce differential effects on cellular behavior. This can form the basis of therapeutic intervention.
5) The subset of TRs expressed by any AP cell is expected to include TR not expressed by the corresponding normal cells and/or conversely. These TRs within the AP cells will be normal TRs ectopically expressed or modified (alternate splicing promoter use or post-translational modification) or mutated to a TR with altered binding properties.

It follows from the rationale given herein that—for any given AP disease made up of disease variants that contain AP cells that have distinctive phenotypes of pathological significance—that these distinct phenotypes will have correspondingly variant patterns of TR expression. In cancer, for example, malignant cells with a multidrug-resistant phenotype would be expected to have a somewhat different pattern of TR expression than drug sensitive malignant cells. However, these variant phenotypes, such as multidrug resistance, should be considered as being an instance of AP cells expressing a subprogram of the greater malignancy program that produces cancer. It should be possible, therefore, to select and target ODNs separately to the malignancy program or to the multidrug resistance subprogram, for example, by attacking different TRs; or to select ODNs which would simultaneously effect both the cancer per se and the subprogram (which, in this example, is multidrug resistance).

When a chronic AP disease undergoes clinical progression, there is an associated progression in the pattern of some of the TR expressed in the diseased cells, although expression of the majority of TR involved will continue to be unchanged. This program progression has several possible consequences, including the consequence where the AP disease being expressed by the disease cells may become independent of some disease risk factor such as, for example, a mutated oncogene in the case of cancer. This is to be contrasted with what could be called acute AP diseases in which (a) at least one pathological risk factor must be currently acting on the diseased cells to produce the disease; (b) the disease is rapidly produced as a consequence; and (c) the disease involves a re-programming of the diseased cells. Perhaps the best example of this type of disorder are the result of an infection with certain pathogenic viruses (Table XII). It follows from the definition of these disorders as acute AP diseases that certain host cell-encoded regulators of cellular programming are appropriate targets for therapeutic intervention utilizing antisense ODNs disclosed herein, even if said TR do not directly up-regulate the expression of the virus in question. The host cell gene targets likely to be best suited for this purpose are TR and other molecules involved in the control of apoptosis and cellular responses to free radicals (Tables X and XI).

The interpretation of these viral diseases as being acute AP diseases leads to an important conclusion. That is, it will be possible to inhibit the expression of a TR encoded by the host cell where said TR is involved in controlling the cellular programming of that cell, such as, for example, by exposing that host cell to an antisense ODN directed to the particular TR in question, the antisense ODN being used either alone or in combination with an augmentation agent such as, for example, an anti-oxidant or an interferon. The impact of this ODN treatment on the programming of said cell will be different when comparing an uninfected with a similar cell expressing the infecting virus. The choice of antisense ODN for the purpose of this invention will be one that exploits this difference to a therapeutic advantage, such as, for example, blocking the ability of a virus to induce apoptosis. Thus, as in the case of the chronic AP diseases, this situation provides the basis for the novel approach to the development of therapeutic agents as described herein.

Nature of Targets

TRs are the primary targets for therapeutic manipulations based on the model. They may be manipulated directly or indirectly through molecules such as tyrosine kinase, that can effectively change a TR of one type to another through structural alterations such as phosphorylation.

While all the TR that are involved in cellular programming are, in accordance with the present invention, potential targets for therapeutic antisense ODNs for the disease(s) in which they are expressed, some TR appear to be more likely than others to be highly useful. There is growing evidence, for example, that many (if not all) of the chronic AP diseases frequently share a common type of insult which contributes to the pathogenesis of the disease. This insult consists of an attack on cells by oxygen free-radicals. In AIDS, for example, there is evidence that HIV-infected lymphocytes undergo apoptosis following exposure to free-radicals (Sandstrom et al., AIDS Res Human Retroviruses 9: 1107, 1993) At least in part this induction of apoptosis is mediated by lipid peroxidation (Sandstrom et al., J Biol Chem 269: 798, 1994). This general conclusion about AP Diseases suggests that (1) those cellular program regulators (TRs, in particular) that are involved with cellular responses to free-radicals should be given priority for testing as targets for antisense ODN inhibition in accordance with the concepts presented herein; and (2) there is a rationale for adding a free-radical generator or an antioxidant, whichever is appropriate, with one of the antisense ODNs disclosed herein for the treatment of an AP disease. Furthermore, these same pathways may also be activated by at least some pathogenic viruses that produce acute disease.

The free-radical generator could be used as an "augmentation agent" in combination with an antisense ODN designed in accordance with the present invention in diseases where the objective is to kill the AP cell (for example, atherosclerosis, or cancer) while the antioxidant would be appropriate as an augmentation agent where the objective is to block apoptosis (for example, AIDS). An antioxidant would be appropriate, also, in the latter cause, because many types of ODN themselves induce cells to generate free radicals. Free radical generators include, but are not limited to, certain polyunsaturated fatty acids (including gamma linolenic acid, eicosapentaenoate and arachidonate), chemotherapeutic agents and ionizing irradiation. Antioxidants include, but are not limited to, certain vitamins, minerals, trace elements and flavinoids. A complete listing of antioxidants would include those known to those skilled in the art, and may be found in standard advanced textbooks, such as, for example, Zubay G L: "*Biochemistry*" (3rd edition), in 3 Volumes, Wm C Brown Communications, Inc., 1993; and in: Rice-Evans CA and Burdon R H (eds): "*Free Radical Damage and Its Control*", New York: Elsevier, 1994; and in: Yagi K et al (eds): "*5th International Congress on Oxygen Radicals and Antioxidants*", New York: Excerpta Medica Press, 1992 (International Congress Series, No. 998). A partial listing of anti-oxidants that have been used clinically include, but are not limited to: ascorbic acid (vitamin C), allopurinol, alpha- and gamma-tocopherol (vitamin E), beta-carotene, N-acetyl cysteine, Desferol, Emoxipin, glutathione, histidine, lazaroids, Lycopene, mannitol, and 4-amino-5-imidazole-carboxamide-phosphate. The choice of which anti-oxidant(s) to use (if any) in conjunction with a particular antisense ODN can be determined on an ad hoc basis by one skilled in the art.

The principal effects of free-radical generators or antioxidants on cells from the perspective of the AP model is to produce an alteration in the pattern of TR being expressed, or, in the case of antioxidants, to prevent the effects on cells produced by cellulariy-generated free radicals subsequent to ODN binding. It follows from the AP model that this pattern will be different following treatment with these "augmentation agents" when normal cells are compared with AP cells.

Hence, it is possible to combine this treatment with an antisense ODN selected according to the criteria given herein (for example, in the Reprogramming Test) and expect different results for normal versus AP cells.

The TR that are known to be involved in cellular responses to free-radicals and apoptosis include, but are not limited to: the AP-1 group, including junD; the Egr group; gadd group; Hox group; IRF group; the MAD-, Max- and Mxi-groups; myc- and myb-groups; NF-kB group; p53; Ref-1; Sp-1; TR-3 and TR-4; and USF (for a more comprehensive list of TR, see Tables II and X). Other genes involved include those directly involved in the regulation of apoptosis, and are shown in Table XI.

It should be noted also that AP cells with major phenotypic differences in accordance with the AP model would be expected to have correspondingly somewhat different patterns of TR expression. One example is the multidrug resistance phenotype that is expressed by a substantial percentage of human cancer cells. Hence, it should be possible in accordance with the present invention to select antisense ODNs (preferably those directed to a TR involved in the maintenance of the multidrug resistance phenotype) and preferentially sensitize multidrug resistant cells to chemotherapeutic agents without getting a correspondingly increase in sensitivity to drug by drug sensitive cells.

Nature of Therapeutic Intervention

The basis of the novel therapy is to differentially change the pattern of gene expression in AP cells by altering the pattern of TR expression. The model states that the specific functional consequences of the expression of any given TR is context-dependent. It therefore follows that the same TR present in both normal and AP cells can be manipulated in the same way and a different impact on cellular behavior obtained. A TR expressed only by the AP cells, however, also may be targeted. The end result is that the pattern of gene expression in the AP cells lose at least a substantial portion of their disease-producing activity. This can be manifested in numerous possible ways including death of the AP cells, a change in their differentiation status with a concomitant change in the production of disease-producing factors or to a loss of proliferative potential.

The number of transcriptional regulators that will have to be manipulated in any given cell type will be very small. There are estimated to be 30,000 to 100,000 genes in the human genome distributed over $3 \times 10^9$ bp of DNA. In any given cell type approximately 10,000 genes can be shown to be expressed. Greater than 90% of these are expressed by many cell types and the large majority of these are referred to as "housekeeping genes."

Typically, the number of genes that can be shown to be differentially expressed in any given cell type account for only a few hundred. It is these genes that make the difference between liver cells and brain cells, for example. The large majority of these are directly involved in carrying out the functions that characterize the cell type. Liver cells, for example, express a wide range of enzymes that are involved in ridding the body of many types of chemicals. The genes of interest for the purposes of this patent are the small subset of genes coding for molecules involved in the differential regulation of cell type specific genes. In particular, transcriptional regulators and their direct modulators. The latter includes, for example, certain tyrosine kinases, that can modify a particular transcriptional regulator and, in effect, change it to a functionally different transcriptional regulator. (Berk Biochem Biophys. Acta. 1009, 103, 1989) For the purposes of this invention transcriptional regulators are defined as molecules that bind to specific DNA sequences variably expressed by different genes and/or to other transcriptional regulators at least one of which must bind to specific DNA sequences. As a result they control the levels of gene expressions by means of modulating RNA polymerase activity. The transcriptional regulators may be of either endogenous or exogenous origin. They may either be normal or be mutated.

The ability of transcriptional regulators to variably interact with each other provides the basis for a combinatorial regulatory system. This allows a very small number of transcriptional regulators to control the expression of a large number of genes in various patterns. Particular sets of genes being controlled at any given time by a certain subset of the transcriptional regulators being expressed by the cell. Each transcriptional regulator subset, therefore, is a programming code or an instruction or a "word" that directs the expression of a particular gene set. The entire pattern of gene expression being expressed by a given cell type can be thought of as a sentence, since only certain words can appear together. Perhaps the first demonstration of the involvement of combinatorial regulation in the control of a cellular differentiation program was provided by Chalfie and his colleagues as part of their studies of C. elegans (Mitani et al., Dev. 119: 773, 1993).

A general role for combinatorial regulation being involved in eukaryotic gene expression has been previously postulated by several investigators. (Scherrer, and Marcand J. Cell Phys 72, 181, 1968; Sherrer Adv. Esp. Med. Biol. 44, 169, 1924; Gierer Cold Spring Harbor Symp Quant Biol 38; 951, 1973; Stubblefield J. Theor Biol 118,129, 1986, Bodnar J. Theor Biol 132, 479, 1988) Lin and Riggs (Cell 4, 107, 1975), demonstrated using biophysical arguments the impossibility of having a separate regulator for every gene in a eukaryotic cell. Combinatorial regulation models of eukaryotic gene expression generally postulate multiple levels of regulation in addition to transcription. In principle, these models show how theoretically 100,000 genes could be selectively controlled by as few as 50 regulatory molecules only a small subset of which would operate at the level of what is defined here as transcriptional regulators. Bodnar J. Theor. Biol. 132, 479, 1988. The actual number of human transcriptional regulators are estimated to number on the order of somewhere in excess of 100. (Table II lists those that have been described in the literature.) Many, however, are known to be expressed only in certain cell types. Since just a few hundred genes determine the differences between particular differentiated cell types and the large majority of these determine the particular functional features of the cell, only a very small number of these can be regulator gene products.

It follows, therefore, that the number of regulators that must be manipulated to achieve the effects stipulated by this invention for any given application is small and can be managed with comparatively modest effort. It also follows from the notion of combinatorial regulation that not all the transcriptional regulators expressed by a given cell type need to be known before this invention can be practiced.

The present inventor has found that antisense p53 oligonucleotides can inhibit the proliferation. including the blocking of stem cell self-renewal, and ultimately kill primary human leukemic blasts while not producing similar effects on fresh normal bone marrow cells. This unobvious result indicates that the interactive mechanisms for detecting, interpreting and responding to environmental informational molecules involved in regulating cell differentiation and proliferation and viability in AP cells are so altered from normal in terms of their dynamic interactions (involving signal transduction and interpretation) that the inhibition of a single gene or set of genes coding for proteins involved in this process by antisense oligonucleotides is sufficient to change the impact of the informational molecules so a change in cellular programming such as cellular death or growth inhibition program can be selectively instituted in AP cells. The term "traitor genes" is used herein to describe those genes in AP cells that may be suitable for targeting for inhibition with antisense molecules in accordance with the present invention Suitable target or traitor genes may themselves either be functionally abnormal or be normal but function to maintain the pathological phenotype AP cells as part of an abnormal pattern of gene expression. Such treatment results in differential programming of AP cells, but not their normal counterparts over a selected dose range. In the preferred embodiment the Traitor Genes to be targeted are TRs.

The concentration of oligonucleotide to be used may vary, depending upon a number of factors, including the type of cancerous cells present in the marrow, the type, and the specificity of the particular antisense oligonucleotide(s) selected, and the relative toxicity of the oligonucleotide for normal cells. Although the present inventor has observed significant AP cell programming at oligonucleotide concentrations in extra-cellular fluid as low as 1 nanomolar, optimal inhibition was observed at concentrations of at least 10 nanomolar in the model system described below. The upper limit of the dosage range is dictated by toxicity and therapeutic efficacy, and, generally will not exceed 5 micromolar. With the aid of the techniques set forth in the present disclosure, those of skill in the art should be able to determine the optimal concentration to be used in a given case.

Phosphorothioates are currently the preferred chemistry for antisense ODNs to be used clinically. A substantial body of pharmacological/toxicological data for this class of compounds shows that phosphorothioates generally behave in a manner similar to most conventional drugs that are used systemically. As a result, the basic pharmacologic principals that have been established over the years apply here as well. For example, see the standard textbook: "*Principles of Drug Action: the Basis of Pharmacology*", 3rd Edition (W. B. Pratt and P. Taylor, eds). New York: Churchill Livingston, 1990. Thus, no novel pharmacologic principles or procedures have had to be invented in order to adapt phosphorothioates to in vivo use. There are some quantitative differences between phosphorothioates and more conventional drugs in terms of in vivo properties, but these differences can be accommodated to particular needs by one with ordinary skill in the art by an application of existing knowledge. In the future, undoubtedly, clinically-superior ODN backbones will be identified and/or developed. The "hotspots" for targeting specific genes and the prototype ODNs revealed herein should work equally well with any improvements in ODN backbone chemistry.

For the immediate purposes of this invention, phosphorothioate antisense ODNs can be administered intravenously (i.v.), intraperitoneally (i.p.), subcutaneously (s.c.) or intramuscularly (i.m.), in order to treat systemic disease. Pendent groups may be attached to the ODNs to aid tissue-specific targeting, or the ODNs may be associated with carriers that facilitate uptake, such as liposomes or charged lipids; in general, however, such modifications will not be necessary. Antisense ODNs can be delivered intrathecally or used in combination with agents that interrupt the blood-brain barrier in order to treat conditions involving the central nervous system. For local therapeutic purposes, phosphorothioates can be applied topically in an appropriate vehicle or delivered to particular organs or tissues by catheters (or catheter-like devices) designed to direct the flow of these compounds to particular sites in the body. Phosphorothioate antisense ODNs may also be administered orally, associated with one or more appropriate and acceptable carrier molecules or compounds, processed for oral ingestion in the form of a tablet, capsule, caplet or liquid. As described elsewhere herein, it may also be desirable to administer the antisense ODN with other active agents. For example, it may be desirable to add an antioxidant to an antisense ODN preparation, or to administer both antioxidant and antisense ODN simultaneously, to treat cancer patients whose tumors express a multidrug resistance phenotype; or to treat AIDS patients when the ODN backbone being employed is known to induce cells to generate free-radicals. Free radicals can induce cells to express higher levels of multidrug resistance, or boost the expression of HIV, respectively.

The extracellular concentrations that must be generally achieved with highly active phosphorothioate antisense ODNs is believed to be in the 10-1000 nanomolar (nM) range. These levels can readily be achieved in the plasma, for example, by infusing phosphorothioates into patients at a rate of a few milligrams per kilogram body weight per hour over a period of a few days. The infusion rate will typically be higher for cancer patients because they have higher levels of an as yet uncharacterized plasma protein that tightly binds phosphorothioates. As for many drugs, dose schedules for treating patients with phosphorothioates can be readily extrapolated from animal studies.

For ex vivo applications, the concentration of the antisense ODN(s) to be used is readily calculated based on the volume of physiologic balanced-salt solution or other medium in which the tissue to be treated is being bathed. In the large majority of applications, the phosphorothioates can be assumed to be stable for the duration of the treatment. With fresh tissue, 10-1000 nM represents the concentration extremes needed for an antisense phosphorothioate ODN with a reasonably good to excellent activity. Two hundred nanomolar (200 nM) is a generally serviceable level for most applications. Incubation of the tissue with the ODN at 5% rather than atmospheric (ambient) oxygen levels may improve the results significantly, except for unusual situations (such as bone marrow or peripheral stem cell purging with antisense ODNs directed to p53) where generation of highly-reactive free radicals appears to contribute to the desired therapeutic effects.

For some therapeutic applications, it may be preferable or even necessary to administer the antisense ODN with another augmentation agent. "Augmentation agents" as defined herein are those agents that can alter patterns of transcriptional regulator expression may include, but are not limited to: cytokines, cancer chemotherapeutic agents, neuroleptics, anti-inflammatory agents, anti-oxidants and free-radical generators such as certain polyunsaturated fatty acids. The suitability of such potential combination treatments generally can be determined initially in the "Reprogramming Test" prior to studies in animal model systems. It is also clearly desirable to add to the assay medium in the Reprogramming Tests of said cells any cytokines which may be associated in vivo with the diseased cells, in order to better model in vivo conditions. The association of particular cytokines with particular disease processes, or the usefulness of particular cytokines in clinical procedures has been well described in such standard reference works as: Thomson A W (Ed) "*The Cytokine Handbook*" (2nd Edition), San Diego: Academic Press, 1994; Kunkel S L and Remick D G: "*Cytokines in Health and Disease*", New York: Decker, 1992; and Oppenheim J J et al (Eds), "*Clinical Applications of Cytokines*", New York: Oxford Press, 1993. The choice of particular cytokines as augmentation agents for a particular disease application is to be limited to those cytokines to which the disease and cells in question respond. Cancer chemotherapeutic agents and free-radical generators could be used as augmentation agents in applications where the objective is to destroy the diseased cells, such as in, for example, cancer and atherosclerosis. Anti-inflammatory agents and anti-oxidants could be used as augmentation agents where the objective is to maintain the viability and/or reduce the pathogenicity of the diseased cells, such as in, for example, AIDS, Alzheimer's Disease, and autoimmune diseases. Neuroleptics could be used as augmentation agents in the treatment of diseases such as schizophrenia, where they have already shown activity.

"Hardware" for Reduction to Practice

Using established techniques, assays and agents, the following capabilities can be readily acquired. These can be used by anyone skilled in the art to reduce the primary and collateral inventions to practice.

1) Assays for transcriptional regulators and their direct modifiers.

Preferred assays: RNA in situ hybridization (Lum Biotech. 4, 32, 1986) or PCR (Block. Biochem 30, 2735, 1991) or metabolic labelling (Ausubel et al (eds.) Current Protocols in Molecular Biology, John Wiley N.Y., 1989 (updated semiannually)) for detecting expression at the protein level.

Purposes:

To establish the subset of the known transcriptional regulators or their direct modifiers that are expressed by a particular cell type. This will serve the following functions:
  a) the determination of the subset of transcriptional regulators, or their direct modifiers, that are targets to be manipulated in the reduction to practice;
  b) the evaluation of the effectiveness of potential therapeutic agents in adding or subtracting the expression of a particular transcriptional regulator or its direct modifier cells;
  c) the diagnosis and/or staging of a particular aberrant program disease;
  d) the determination of the optimum therapeutic agent(s) in clinical practice, when there are more than one option for a given disease.

2) Agents for adding or subtracting the expression of particular transcriptional regulators or their direct modifiers in cells to be therapeutically manipulated.
  a) Antisense oligonucleotides (Zon, Pharmaceut. Res., 5, 539, 1988).

These agents can be used to subtract the expression of particular genes from cells. Antisense oligonucleotides can produce an induction of their target gene by inducing an induction of their targe gene by inducing an initial reduction in expression that is then over compensated for as a consequence of a feedback loop in the cells or by altering the half-life and/or translational rate as a consequence of the antisense oligonucleotide producing a change in the target RNA secondary structure and/or by altering the binding of regulatory molecules to the target RNA. Such an action by antisense oligonucleotides is suitable for the practice of this invention.

Design of "Test" Antisense Oligonucleotides i) Using a computer program such as "Oligo" (Rychik and Rhoads, Nucl. Acids Res., 17, 8543, 1989) select a set of antisense oligonucleotides that bind to the RNA target of choice that have the following characteristics: (1) length between 10 and 35 bases with 20 being generally used; (2) negligible self-interaction (self-dimers and hair pins) under physiologic conditions; (3) melting temperature $\geq 40°$ C. under physiological conditions; and (4) no more than 40% of the oligonucleotide being a run of guanines or cytosines);

ii) Using a reference such as Genbank ensure that the antisense oligonucleotide has $\leq 85\%$ homology with the RNA transcripts of other genes. An exception to this is where an antisense oligonucleotide is selected on the basis of its ability to bind to more than one member of a transcriptional regulator family (such as the homeobox genes) on the basis of sequence homology.

b) Establishment of "prototype therapeutic" antisense oligonucleotide from a set of test antisense oligonucleotides. These prototype compounds will be used in the reduction to practice.
  i) Synthesize test antisense oligonucleotides using standard procedures, for example, those for producing phosphorothioates (Vu et al, Tetrahedron Lett, 32, 3005, 1991).
  ii) Using assays for transcriptional regulators or their direct modifiers select prototype therapeutic antisense oligonucleotides out of the set of test compounds on the basis of shutting down expression of the target gene in the cell types to be therapeutically manipulated. In practice, the same set of prototype agents capable of shutting down target gene expression in a variety of cell types could be used in the Reduction to Practice, Step 2, hereinafter, for multiple therapeutic objectives.

b) Synthetic double-stranded oligonucleotides that are ligands for the DNA binding domain of one or more transcriptional regulators. (Wu et al, Gene, 89, 203, 1990)

Prototype therapeutic agents of this type for use in the reduction to practice will correspond to actual gene sequences to which the transcriptional regulator(s) will have been shown to bind using standard techniques such as the gel mobility shift assay. (Ausubel et al (eds.) Current Protocols in Molecular Biology, John Wiley N.Y., 1989 (updated semiannually).) Alternatively, single stranded oligonucleotides targeted to transcriptional regulator binding sites and the adjacent sequences can also be used to block the expression of particular genes in accordance with the present invention.

c) Expression vectors

In the preferred embodiment a recombinant viral vector will be used (Miller and Rosman, Biotech, 7, 980, 1989) that carries the complete coding sequence of the transcriptional regulator or its direct modifier. This will provide for expression of the regulator or modifier in the cells of interest. It will be constructed and tested using standard methods. (Ausubel et al, supra) Alternatively, the viral vector will carry a sufficiently long antisense sequence to such a regulator or modifier to provide for the blocking of expression of the target gene in the cells of interest.

3) Preparation of Tissue

The preferred tissue is primary explant or early passaged. It will be acquired using standard surgical procedures. Tissue processing for culture and/or heterotransplant will be according to established methods. Culture conditions for the disordered cells from the various aberrant program diseases or their normal counterparts are referenced in Table III. These references also provide information on acquiring and processing the appropriate cells.

Uses to provide the source material for:
a) determining the subset of the known transcriptional regulators or their direct modifiers that are expressed by a particular cell type.
b) practicing the collateral inventions; that is, diagnosis and staging an aberrant program disease or for selecting optimal treatment in clinical practice.
c) evaluating possible adverse effects of treatments for aberrant program diseases on cultures of the three major constitutively self-renewing tissues (bone marrow, gastrointestinal epithelium, and skin). These cultures will also be used in some of the reductions to practice involving therapeutic manipulations of normal tissue. Culture conditions, Table IV.
d) The other cultures and heterotransplants to be used in the reduction to practice.

4) Discrimination of normal vs malignant cells in a mixed population.
Standard in situ hybridization procedures for detecting chromosome and/or translocation specific changes will be utilized. (Trask Trends in Genet. 7, 149, 1991).

5) Establish assays for scoring effects of manipulating transcriptional regulator function or their direct modifiers on cellular programming.
a) Aberrant program disease tissue
By definition the affected cells in these disorders express abnormal patterns of gene expression that produce the characteristic clinicopathologic features. Both of these can be monitored using established molecular and cellular techniques. The specific parameters to be assayed for each of the types of aberrant program disease given as examples are shown in Table III.
b) Normal tissue—
Reprogramming normal cell behavior where the relevant programs are differentiation, proliferation and viability could serve a variety of therapeutic uses. These would include but not be limited to certain in vitro and systemic treatments: (1) expansion of normal cell numbers in vitro prior to transplantation; (2) promotion of the growth of gastrointestinal cells in the treatment of peptic ulcers and inflammatory bowel disease; (3) liver regeneration, for example, following partial destruction by a virus or toxic chemicals; (4) expansion of one or more hematopoietic cell lineages for a variety of clinical purposes including reconstitution of immune function in immunodeficiencies, counteracting the effects of agents toxic to bone marrow and in fighting infection.
All of these changes in normal cellular programming can be readily assessed using established techniques.

B) Reduction to Practice
Step 1) Determine the subset of transcriptional regulators, and their direct modifiers, expressed by the aberrantly programmed tissue, the corresponding normal tissue, and the constitutively self-renewing normal tissue. Alternatively make a similar determination for any other normal tissue that is to be therapeutically manipulated in accordance with this invention.
Step 2) Add or subtract expression of transcriptional regulator(s) or their direct modifiers from cells to be therapeutically reprogrammed and the appropriate control tissue, as previously specified.
a) Addition—Use expression vector to insert expressible gene for a particular transcriptional regulator or a direct modifier of a transcriptional regulator into aberrantly programmed cells. The inserted gene will be one that is expressed by the corresponding normal cells, but not by the aberrantly programmed cells.
b) Subtraction—
i) can be achieved by the use of antisense oligonucleotides directed to the RNA of a particular transcriptional regulator or direct modulator or double-stranded oligonucleotide ligands for DNA binding domain of one or more transcriptional regulators
Using prototype antisense oligonucleotide(s) or double-stranded oligonucleotides block function of specific transcriptional regulator(s) in aberrantly programmed cells or normal cells to be therapeutically manipulated through reprogramming. Alternatively use an antisense oligonucleotide directed to a direct modifier of a transcriptional regulator.
ii) Using expression vector carrying antisense DNA directed to a particular transcriptional regulator or a direct modifier of a transcriptional regulator, install the new gene in aberrantly programmed cells. The therapeutic effect will be determined in advance through the use of an antisense oligonucleotide.

Step 3) REPROGRAMMING TEST:
Using the methods and procedures described in the "Hardware for Reduction to Practice" and using the information given in Tables III and IV, perform the following functions.
a) Utilize appropriate culture conditions for normal cells to be therapeutically reprogrammed or for AP disease, the AP cells plus the corresponding normal cells and constitutively self-renewing normal tissues (gastrointestinal, bone marrow, skin);
b) For AP disease, assay one or more pathogenic features of AP cells such as those shown in Table III and described in references in Table XIII, according to established procedures;
c) Treat cultures with prototype agent with reprogramming potential (as oligonucleotides to TR, as oligonucleotide ligands for TR, or expression vectors).
d) Score changes in programming and choose those agents that are therapeutically useful; for example:
1) cancer, myelodyspl asia and myeloproliferative-syndromeandatherosclerosis-kill AP cells;
2) AIDS, regenerate $CD4^+$ lymphocytes;
3) Expand normal hematopoietic stem cells for bone marrow transplant.
4) Alzheimer's cells: block apoptosis;
5) Rheumatoid arthritis: block inflammatory responses, and block joint destruction;
6) Schizophrenia: monitor in vitro predictors of potential for altering nervous system functioning to improve cognitive state of patients;

Step 4) Test effect of addition or subtraction of the function of particular transcriptional regulators using the agents selected in an animal model system if the therapeutic agents are for systemic use. (Table XIII)
Because of the need for a high degree of target homology with the corresponding human transcriptional regulator or its direct modulator the animals will of necessity nearly always be non-human primates. Immunocompromised animals xenotransplanted with human tissue are also of value for in vivo efficacy studies.
In the case of evaluating agents for the treatment of aberrant program diseases the animal may either be afflicted with the disease and both the efficacy of the treatment and the side effect documented or the animal may be normal and only the side effects tested.

Step 5) Any undesirable side effects that might be produced by the potential therapeutic agents can be reduced or eliminated in several possible ways, all of which can be implemented using existing technology.

a) Antisense oligonucleotides

FIG. 1 demonstrates that there are cell type specific differences in effects of particular antisense oligonucleotides targeted to different sites on specific RNA transcripts on cell behavior. Such differences can be used to select antisense oligonucleotides that produce the desired therapeutic effects with minimal undesirable side effects. These differences could be due to several factors, including differences in the availability of particular "hotspots" for antisense ODN binding between different cell types/specimens, aptameric or backbone effects.

b) Double-stranded oligonucleotide ligands Typically more than one transcriptional regulator can bind to the same double-stranded DNA sequence, but with variable affinities. It is, therefore, possible to change the competitive inhibitor effect of such an agent relative to the potential set of target transcriptional regulators by introducing base changes. These can include mismatches. The melting temperature of the two resulting strands, however, must be $\geq 40°$ C. under physiologic conditions. The effect of such changes, therefore, can produce a more favorable therapeutic index.

c) Expression vectors

The levels of expression and efficiency of gene transfer can be readily adjusted on a tissue specific basis by changes in the viral envelope and/or the promoter/enhancer combination used to achieve gene expression.

The forgoing, then, can be reduced to a novel "Method of Rational Discovery" for antisense oligonucleotides for the treatment of Aberrant Programming disease comprising the following steps:

(i) select one or more transcriptional regulator gene targets implicated in the regulation of cellular programming in the Aberrant Programming Disease, these targets also being expressed by the diseased cells to be reprogrammed;

(ii) select one or more prototype antisense oligonucleotides to target transcripts of the selected transcriptional regulators, where the prototype antisense oligonucleotides are chosen from among those targeting gene "hotspots" defined by the Tertiary Selection Method, as described hereinafter;

(iii) evaluate the prototype antisense oligonucleotides in the Reprogramming Test for their capacity to therapeutically reprogram the Aberrant Programmed disease cells while at the same time not adversely reprogramming normal cells;

(iv) combine the selected prototype antisense oligonucleotide with another augmentation agent which is capable of altering the pattern of transcriptional regulator expression through a change in the expression of or physical state of the TR, where the TR is expressed in the Aberrant Programmed cells, to discover if the agent improves the ability of the selected antisense oligonucleotide to therapeutically reprogram the Aberrant Programmed cells;

(v) design sequence- and length-variants of the selected prototype antisense oligonucleotides which scored well in the Reprogramming Test (i.e., which exhibited capacity to reprogram Aberrant Programming cells); the variants should be selected so that they bind to sites overlapping or contiguous to the binding site of the corresponding prototype antisense oligonucleotide, and have negligible capacity to form self-complementary dimers or hairpin structures;

(vi) evaluate these variant ODNs alone, or with the agent selected in step (v), in the Reprogramming Test for capacity to effectively reprogram the Aberrant Programmed disease cells in the Aberrant Programming Disease while not adversely reprogramming normal cells; and then (vii) test the most active of the evaluated antisense oligonucleotides, either alone or with the agent selected in step (v), for therapeutic efficacy in an animal model system if the therapeutic agents are for systemic use.

(viii) evaluate the data, and select the antisense ODN which exhibits the best therapeutic index with the least toxicity, for potential use as a therapeutic agent in clinical trials.

Demonstration of the Reduction to Practice with a P53 Target

Step 1—

It is known that p53 is expressed by primary human leukemia blast cells using the metabolic labeling technique (Smith, et al., J. Exp. Med. 164, 751, 1986.)

Step 2—

A set of four different phosphorothioate antisense oligonucleotides directed to p53 RNA were prepared using an Applied Biosystems, Inc. (ABI) DNA synthesizer (Model 380B) according to the manufacturer's protocols. An antisense oligonucleotide against the HIV rev gene was used as a negative control. The sequences are set forth in the Sequence Listing hereinafter as SEQ ID NOS: 1-4. These were used to treat primary human leukemic blasts, normal human bone marrow, normal human circulating T-lymphocytes, normal adult human gastrointestinal epithelium, normal human fetal gastrointestinal epithelium and Rhesus monkey T-lymphocytes. Destruction of p53 RNA by the antisense p53 oligonucleotides was documented using PCR and/or dot blotting.

The four p53 sequences are as follows:

```
SEQ ID NO.1:    5'-AGTCTTGAGC ACATGGGAGG-3'    C(1)p53

SEQ ID NO.2:    5'-ATCTGACTGC GGCTCCTCCA-3'    A(1)p53

SEQ ID NO.3:    5'-GACAGCATCA AATCATCCAT-3'    A(3)p53

SEQ ID NO.4:    5'-CCCTGCTCCC CCCTGGCTCC-3'    OL(1)p53
```

Step 3—

The following effects of the antisense p53 oligonucleotides on cellular programming were evident from the results found.

1) They can irreversibly block the proliferation of, block stem cell self-renewal, or kill human cancer cells. This coupled with the lack of toxic effects on normal tissue indicates these agents can have a role in the treatment of cancer. (See Tables V-VIII).

2) They promote the proliferation of gastrointestinal epithelium, indicating a role in the treatment of peptic ulcer and inflammatory bowel disease (FIG. 1). The suppressive effect of these agents on mature lymphocyte (Table IX) proliferative also supports their role in diseases such as inflammatory bowel disease that have an autoimmune component.

3) The data also demonstrates that there are cell type specific differences in responses to antisense oligonucleotides targeted to different sites on RNA transcripts of the same gene (FIG. 1). This provides a basis for optimizing therapeutic effects and for minimizing undesirable side effects.

4) These results support the general principle that antisense oligonucleotides directed to a transcriptional regulator can be used to expand particular normal adult or fetal tissues in vitro that could then be used for various medical purposes including transplantation (FIG. 1).

5) The cell type dependency of the effects of particular antisense oligonucleotides directed to a transcriptional regulator support the cellular program model in general and the aberrant program model in particular.

Step 4—

The ability of the antisense p53 oligonucleotides to recognize the p53 RNA of Rhesus monkeys was demonstrated by showing a similar inhibitory effect on mature T-cell proliferation for both Rhesus and human cells (Table IX).

Two Rhesus monkeys weighing 8.9 kg and 6.8 kg were infused with 52.5 mg and 75.8 mg of the OL(1)p53 antisense oligonucleotide (SEQ ID NO:4) which was radiolabeled over four hours. In keeping with rodent data, tissue distribution analysis showed substantial oligonucleotide uptake compared to the levels needed to block p53 expression. Excretion studies demonstrated retention of the infused agent for more than two weeks. During this time and subsequently, the animals were extensively monitored for signs of toxicity and none were seen. These and additional results were reported in: Cornish KG, P Iversen, L Smith, M Arneson and E Bayever: *Cardiovascular effects of a phosphorothioate oligonucleotide with sequence antisense to p53 in the conscious Rhesus monkey*. Pharm. Comm. 3(3): 239-247 (1993), which is expressly incorporated herein by reference.

It was not possible to do in vivo efficacy studies with the p53 antisense ODN in an animal model for two reasons: (1) there were no readily-available animal model systems that utilized freshly-obtained human leukemia cells as xenotransplants, including no readily available primate leukemia animal models; (2) there is at best only a modest effect of the p53 antisense ODN on established in-vitro-adapted human leukemia cell lines, in contrast to the significant p53 effects observed on primary (fresh) human leukemia cells in vitro. These latter data were reported in: Bayever E, L Smith et al: *Selective cytotoxicity to human leukemic myeloblasts produced by oligodeoxyribonucleotide phosphorothioates complementary to p53 nucleotide sequences*. Leukemia and Lymphoma 12: 223-231 (1994), which is expressly incorporated herein by reference.

Step 5—

Since no unacceptable side effects were produced in the monkeys, it has not been necessary to modify the antisense oligonucleotides.

Step 6—

The non-toxicity of the antisense p53 phosphorothioate oligonucleotide OL(1)p53 was confirmed after systemic administration into humans in a Phase I clinical trial designed with the review and approval of the U.S. Food and Drug Administration. The initiation of this world's-first clinical trial of systemically-administered antisense ODN was reported by: Bayever E, L Smith et al: *Systemic human antisense therapy begins*. Antisense Res. Develop. 2: 109-110 (1992), which is expressly incorporated herein by reference.

In addition to the treatment of patients with cancer, the p53 antisense ODNs may be used to treat certain other diseases or medical conditions that include, but are not limited to, the following: AIDS; Atherosclerosis/restenosis; Alzheimer's disease; autoimmune diseases including, for example, multiple sclerosis, rheumatoid arthritis, and systemic lupus erythematosus, in accordance with the AP model. The results may be substantially improved by adding either a free-radical generator or an anti-oxidant as augmentation agents, as previously described. In addition, free-radicals may cause an alteration in the conformation of p53, with the result that p53, so altered, can function like an essentially different TR (Maxwell and Roth: Crit. Rev. Oncog. 5: 23, 1994; Hainaut and Milner: Cancer Res. 53: 4469, 1993). In this instance, a free-radical generator or redox modifier used to produce this effect would be a direct modifier of p53. These p53 antisense ODNs, used alone or with an augmentation agent, may also be used to block apoptosis in damaged normal tissue, for example, as a result of blood vessel occlusion and/or reperfusion injury, or ionizing radiation damage to the skin.

Novel Computer-Based Method for Selecting Target Sites for Highly Active Antisense ODNs The four p53 antisense ODNs (SEQ ID NOS. 1-4) mentioned above were all designed using the method described above under the title "*Design of 'Test' Antisense Oligonucleotides*", along with certain other considerations. The general area to which A(1)p53 (SEQ ID NO.2) and A(3)p53 (SEQ ID NO.3) were targeted were, or were thought to be, the translational start site for regular or for alternatively spliced p53, respectively. The practice of targeting antisense ODNs to areas of RNA transcripts thought to have a regulatory role (beyond coding a protein) is well established in the literature. C(1)p53 (SEQ ID NO:1) was targeted to a general area of approximately 150 base pairs (bp) in length that was selected by a computer program designed to pick out potential functional areas in nucleotide sequences. The basis of this latter program is Chaos Theory. This C(1)p53 oligonucleotide binds to one strand of the DNA duplex in the p53 gene that includes a transcriptional regulator binding site.

In contrast, the target area for OL(1)p53 (SEQ ID NO.4) was selected from a group of possible sites within the p53 transcripts, without consideration of whether or not a biologically significant function was associated with any of these regions of the p53 transcript. Instead, the inventor simply further restricted the criteria presented under "*Design of 'Test' Antisense Oligoriucleotides*". The restriction was to obtain an ODN with the highest possible $T_m$ value (equivalent to lowest $\blacktriangle G°$ value) without compromising the other selection criteria. In subsequent discussions which follow, the originally-described selection method and criteria under the title "Design of 'Test' Antisense Oligonucleotides" will be termed "the primary selection method", while the method with the more restricted criteria to be described next will be termed "the secondary selection method." Again, it was this secondary selection method that was utilized to design OL(1)p53.

The "OLIGO" computer program (Version 3.4), created by Dr. Wojciech Rychlik (Rychlik and Rhoads, Nucleic Acids Res. 17: 8543, 1989; copyright 1989), was utilized in all of the hotspot selections included herein. This is the same "OLIGO" computer program originally used by the present inventor to examine the p53 cDNA sequence. The p53 sequences were examined using computer-generated probe of all possible antisense ODNs containing 20 nucleotide bases (i.e, a "20-mer") that could bind with the p53 cDNA. The inventor instructed the computer program to calculate the binding affinities for these antisense ODNs under the conditions of 138 mM salt and an ODN concentration of 250 nM. Next, the inventor asked the computer to list all of the possible 20-mer antisense ODNs that would have negligible self complementarity, which is defined as not having hairpin structures within the 20-mer (neither negative nor positive ▲G° values), and no self dimerization with more than two continuous base matches. Using the "Option 'Z'" function in the "OLIGO" program, the program was then asked to print out a list of the 5-prime terminal base positions of the sites on the p53 sense strand to which the ODNs would bind, the extreme 5'-nucleotide of the entire gene/cDNA sequence as it came from Genbank or the literature being designated nucleotide position number 1. These sites were entered into the primary array of the program's memory. Next, using the memory for the secondary array, all the 20-mer ODNs with a higher binding affinity for their target than a certain value (again, selected by the inventor) were entered. In standard physical chemistry terms, the more negative the value of the ▲G° indicated for a particular 20-mer ODN, the higher the binding affinity to its corresponding target sequence. Therefore, beginning with a ▲G° value of –43.0 kcal per mole (kcal/mol), and then making the ▲G° value more negative in steps of –2 kcal/mol (i.e., for example: –45 kcal/mol, –47 kcal/mol, –49 kcal/mol), the inventor directed the computer to compare primary and secondary arrays and to print out the start sites for all the 20-mers meeting the criteria used in both arrays. The inventor initially decided intuitively that he would assume that the more negative the kcal/mol value for a given 20-mer ODN (i.e., the more tightly it bound to its corresponding target sequence), the higher would be the biological activity of the corresponding antisense ODN. This assumption could then be tested.

Next, the 20-mers meeting the criteria in both arrays were examined to further determine the suitability of these antisense ODNs. Any ODN having four (4) or more guanine bases in a row were eliminated. Originally, this was done because ODNs having four or more guanine bases in a row were thought to be more difficult to synthesize. More recently, however, it has been determined that four guanine bases in a row may cause the formation of a "G-quartet" which, through formation of intermolecular complexes, may cause production of significant adverse, sequence-specific, non-antisense effects on cells. Further, any ODN having ≧85% match (i.e., 17 matches out of 20 bases) with any other known human gene sequence whose blockade by ODN would negatively influence the therapeutic utility of the antisense ODN in question were also eliminated. OL(1)p53 constituted the single 20-mer antisense ODN that met all these individual criterion and which had the most negative ▲G° value (–47.5 kcal/mol) when these criteria were applied to the p53 gene/cDNA sequence (Lamb and Crawford, Mol. Cell. Biol. 6: 1379, 1986).

Finally, the method for selecting antisense ODNs underwent a final stage of development to yield the "tertiary selection method." It is this tertiary selection method that was used to select the many additional "hotspots" and prototype antisense ODNs that are disclosed herein. The tertiary selection method consists of the following steps: (1) the secondary selection method is utilized to find the binding sites for the ODNs that have a high probability of being the most active, with one modification: i.e., 22-mer lengths of ODN rather than 20-mer was used for probing the target gene sequences. This was accompanied by a decrease in the required –kcal/mol value for binding affinity to –45.0 kcal/mol for primary hotspots. Identification of a continuous and contiguous run of 5'-end starting positions on the computer print out was considered to reveal the core of a "hotspot" for antisense ODN targeting. Using the OLIGO program in the manual mode, examining contiguous overlapping binding sites on either side of the "core hotspot" for self-complementarity, potential antisense ODNs varying in size from 16-27 nucleotides in length were identified. Of these, ODNs contiguous with the core hotspot were rejected if they were shown to contain sequences which would generate a stable self hairpin structure with a negative ▲G° value (<1.0 kcal/mol) as calculated by the OLIGO program, and/or if the ODN was estimated to have significant self dimerization at 37° C. (Self dimerization is most readily evaluated by using the upgraded OLIGO program in Version 4.0). Once all of the acceptable contiguous ODNs are determined by this procedure, then the "hotspot" has been defined. As a rule of thumb, the present inventor has determined that if 10 such hotspots can be identified for a particular gene target, then one should find that at least three (3) of these sites will yield very highly active antisense ODNs, and this probability is inversely correlated with the calculated –kcal/mol binding affinity for the antisense ODN in question. Most of the prototype antisense ODNs designed by the inventor for the evaluation of these hotspots are 22-mers that optimize minimal self interaction with a large –kcal/mol value. In some instances, these parameters can best be optimized by going to a longer or a shorter antisense ODN. Multiple active antisense ODNs within any given "hotspot" are needed for several reasons, including the possibility that some ODNs will have unexpected but biologically important aptameric (or aptameric-like) effects which may either increase, decrease, or have no effect on the therapeutic endpoint to which the antisense ODN in question is directed.

Not all gene targets will yield 10 or more hotspots according to the criteria just presented. In these cases, additional ("alternative" or "secondary") hotspots can be found by manually examining each of the areas of the gene that yield antisense ODNs with the highest binding affinity for their targets as measured by the calculation of the –kcal/mol value (this, too, is to be considered part of the tertiary selection procedure). Each of the potential antisense ODNs in these areas are examined for self complementarity using the aforementioned relaxed standards of no hairpin structures with self-binding affinities of ≦1 kcal/mol or significant self dimerization at 37° C. as judged by the OLIGO program, version 4.0. The set of contiguous overlapping antisense ODNs uncovered in this way then define a "hotspot" within the transcript (sense) sequence. Again, the prototype antisense ODNs selected for each of these hotspots are optimized for two (2) parameters which are minimal self interaction, and a more highly negative kcal/mol value for binding to the target site in the gene transcript.

Using this tertiary selection method, the most highly active antisense ODNs for blocking the expression of particular genes can be discovered. The steps are: (1) design antisense ODNs according to the tertiary selection method; (2) synthesize and test the prototype antisense ODNs for each hotspot; (3) pick the most active prototype antisense ODNs; and (4) design and test new variants derived from these prototypes. The variants should be designed to bind further upstream or downstream of the prototype, in short steps of two or three bases, and variants of shorter or longer lengths varying by two bases at a time should be tested. In an initial test to determine if shortening the ODN improves its antisense activity, or to determine if shifting the ODN two bases downstream improves antisense activity, for example, the subsequent variants that continue in the same direction of change should be evaluated. All of these variants, however, will fit into the range of possible antisense ODNs defined by the corresponding hotspot.

Following standard drug development procedures, these antisense ODNs will be first tested in vitro for activity whenever possible, and for toxicity. Next, in vivo studies of potential efficacy (where there is an appropriate animal model) (Table XIII) and pharmacology/toxicology analyses will be carried out. Antisense ODNs successfully making it to this stage of development will be subject also to any additional studies that might be required by the U.S. Food and Drug Administration for achieving approval of an Investigational New Drug (I.N.D.) application.

Testing of the Novel Computer-Based Method for Selecting Target Sites for Highly Active Antisense ODNs.

Example 1

In vitro comparisons of the relative activity levels of the four p53 antisense ODNs (SEQ ID NOS. 1-4) showed that OL(1)p53 (SEQ ID NO.4) was consistently the most active in terms of producing anti-tumor effects. Freshly obtained acute myeloid leukemia (AML) blast cells, as well as ovarian, colon, lung and brain cancer specimens, were tested. In nearly every experiment in which the four p53 antisense ODNs were evaluated simultaneously on such tumor specimens, the OL(1)p53 antisense ODN exhibited the most potent activity. Activity was determined as a reduction in viable cell counts and by reduced capacity of treated cells to grow in methyl cellulose as colonies in colony forming assays, compared to cells treated with control ODNs. The results with fresh AML blast cells have been published (Bayever et al., *Leukemia and Lymphoma* 12: 223-231,1994). These data were consistent with the notion that the secondary selection method would yield ODN sequences with a greater probability of being the most highly active than selecting ODNs by applying the primary selection method to regions of transcripts thought to have an important regulatory function beyond encoding for a particular protein (such as the 5'-cap site, the AUG start site, or splice junctions).

Example 2

Having discovered a method for selecting highly active antisense ODNs, the present inventor designed a series of antisense ODNs against two other gene targets in order to further test and confirm the value of the selection method herein disclosed. The MDR1 gene that encodes P-glycoprotein, and the gene encoding the multidrug resistance-associated protein (MRP) were selected for these studies. The protein products of these genes constitute molecular pumps that have been implicated in the production of the multidrug resistance phenotype in cancer cells. Hence, antisense ODNs with the capacity to block the expression of these genes would be expected to increase the sensitivity of treated multidrug resistant tumor cells to chemotherapeutic agents such as vincristine, doxorubicin and VP-16. The entire MDR1 gene has been cloned and sequenced, while only the MRP cDNA has been cloned and sequenced. Consequently, there is a much larger number of functional sites that can be targeted on the MDR1 transcript.

The primary selection method was used to design antisense ODNs to target selected regions of the MDR1 transcript; the functional significance of the selected regions had been described (Chin et al., Mol. Cell. Biol. 9: 3808, 1989; Chen et al., J. Biol. Chem. 265: 506, 1990; Kohno et al., J. Biol. Chem. 265: 19690, 1990). These regions included the 5'-cap site, the 5'-untranslated leader, splice junctions and the translational start site (containing the AUG codon). These types of functional sites have frequently been identified as suitable targets by other investigators. In addition, other antisense ODNs were selected using the secondary selection method described herein, and also by the method for finding alternative or secondary hotspots described herein; these ODNs will be discussed hereinafter.

To determine relative activity among the various MDR1 antisense ODNs, they were incubated at several different ODN concentrations in cell culture medium with the human multiple myeloma cell lines 8226/Dox4 or 8226/Dox6 (gifts of Dr. William Dalton, University of Arizona Cancer Center, Tucson) (Dalton et al., Cancer Res. 46: 5125, 1986). Specifically, the human myeloma cells were incubated with the antisense ODNs for four (4) days, in a humidified, 5% $CO_2$ atmosphere containing a reduced oxygen level of 5%, maintained by purging the culture incubator with nitrogen gas in place of ambient room air. Addition of an antioxidant to the cultures during exposure of the cells to the ODN further reduces the effects of the free radicals induced by the ODNs on cells (this effect can include increased expression of MDR1). The cell cultures were then incubated with a chemotherapeutic anti-cancer agent overnight (15-18 hrs), after which the cell cultures were washed repeatedly and then seeded into 96-well microtest plates to permit quantitative analysis of their growth. Tritiated-thymidine was added to these cultures for 18-hrs prior to termination of the assays on day 4 following exposure to the anticancer agents. Each test combination of cells, antisense ODN and anti-cancer agent was run in quadruplicate replicates.

The data for MDR1 antisense ODNs are shown in Table XIV, and show that the most active ODNs were those which had been selected using the secondary selection method. In this Table, the most active MDR1 antisense ODN is OL(1 C)mdr. Re-iterating, the criteria of the secondary selection method (1) permit no self interactions in the ODN (such as hairpin structures) and no more than two contiguous base pair matches in self-dimers; and (2) maximize the negativity of the calculated –kcal/mol value to ensure the most avid binding of the antisense ODN to its corresponding target sequence, without compromising the other criteria provided. These are the same parameters that were used to select the OL(1)p53 antisense ODN (SEQ ID NO.4).

Next, variants of OL(1)mdr and OL(12)mdr—the most active of the antisense ODNs targeting MDR1 transcripts—were tested. The results of one such experiment are shown in Table XV and in FIG. 2. Among the several OL(1)mdr variants, OL(1C)mdr and OL(1 Q)mdr were found to be two of the most active in terms of producing the greatest "fold-increase" in drug sensitivity, when calculated using as the "treatment control" cells treated only with culture media ("Method 2", last two columns, Table XV). If, on the other hand, the "treatment control" cells used in the calculation were cells treated with the corresponding ODN ("Method 1", middle two columns, Table XV), then the OL(1C)mdr variant is calculated to be less active than certain other MDR-ODNs, including OL(12)mdr, OL(12A)mdr and OL(1B)mdr. The OL(1)mdr ODN and its variants were selected using the secondary selection method, while the OL(12)mdr ODN and its variants were selected using the method for finding alternative, or secondary, "hotspots".

Figure 2:
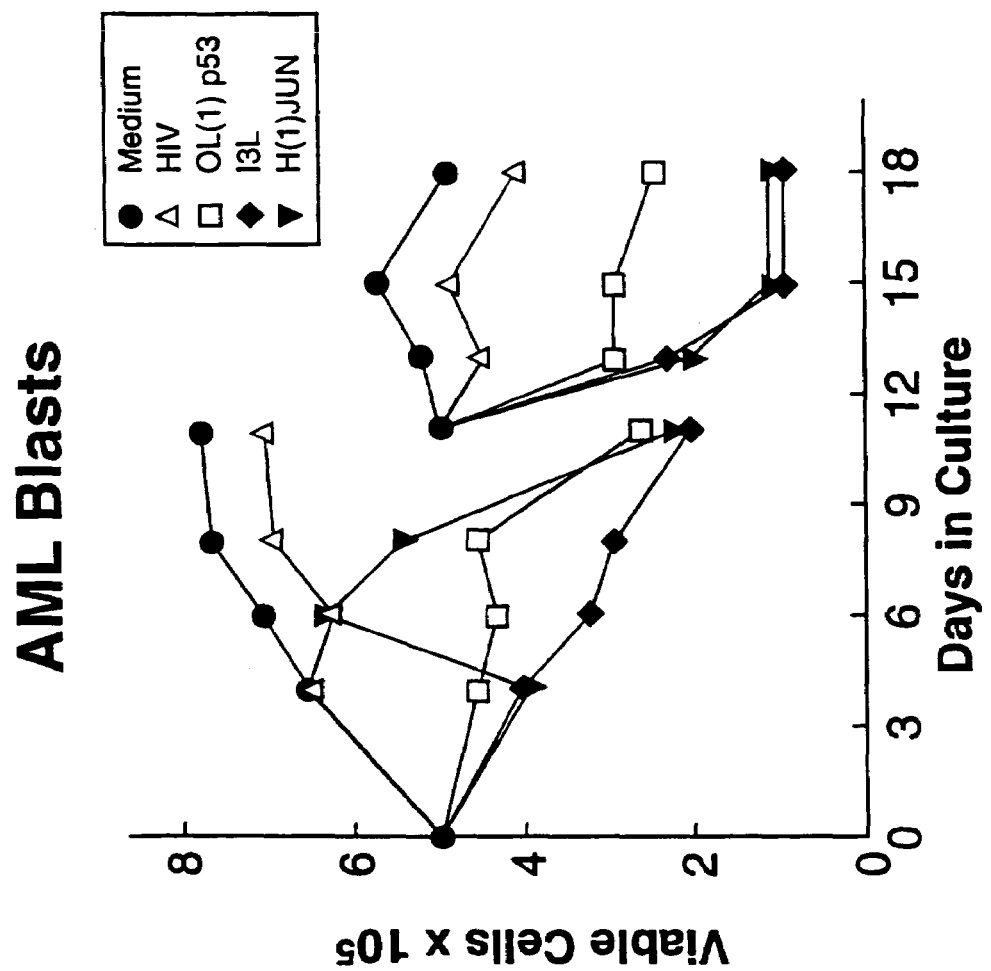
FIG. 2 is a graph showing the effects of different antisense oligonucleotides on viability of AML blasts.

The very high potency of the OL(1 C)mdr prototype MDR-ODN on 8226/Dox4 cells, however, appears possibly to be due to a combined antisense effect on MDR1 transcripts and to an aptameric-like effect that also can cause suppression of MDR1 expression in these highly drug resistant cells. This aptameric-like effect is also associated with a partial inhibition of proliferation of this highly P-glycoprotein expressing cell line (FIG. 2). It is this effect that explains the differences seen with the "Media Control" versus "Corresponding-ODN Control" in calculations of fold-increases in drug sensitivity of ODN-treated cells (Table XVI). A likely explanation for this aptameric-like effect is that the ODNs showing this effect are binding to cellular proteins involved in the regulation of MDR1 expression, such as, for example, protein kinase C and/or protein kinase A.

The enhanced reduction in P-glycoprotein expression due to the combined antisense and aptameric-like effects likely causes the associated reduction in cell proliferation. It has been previously shown that treating P-glycoprotein-expressing cells with monoclonal antibodies capable of binding to and blocking P-glycoprotein function leads to a substantial reduction in the proliferation of the treated cells. The fact that OL(1C)mdr is more active than OL(12)mdr and it variants on cell lines that express less P-glycoprotein (such as 8226/Dox6 and CEM/VLB cells) is consistent with this hypothesis. It is also possible that the aptameric-like effect that leads to a reduction in P-glycoprotein expression also inhibits a cellular pathway involved in proliferation, such as the protein kinase C pathway. The lack of the aptameric-like effect on less drug-resistant cells, or on drug sensitive cells, could reflect the fact that such cells do not have the up-regulated PKC pathway commonly seen in highly drug-resistant cell lines (Table XVII). The relative ranking of the most potent MDR-ODNs was confirmed using less drug-resistant P-glycoprotein-expressing CEM human leukemia cells. The MDR-ODNs showing the aptameric-like effect on 8226/Dox4 cells did not produce this effect on these P-glycoprotein-expressing CEM cells. The term "aptameric-like" is used because the effect seen is seen with some sequences but not others (aptameric); aptameric-like effects are substantially more common among ODN sequences than are the usual aptameric effects. OL(1C)mdr did not produce drug sensitization of drug sensitive lines, and has no significant effect on the proliferation or differentiation of normal human bone marrow progenitor cells in standard in vitro assays. In general, this situation in which the antisense and an aptameric-like effect of an ODN both act to reduce expression of the same gene (e.g., MDR1) can be expected to be a very uncommon finding among antisense ODN therapeutics directed to other gene targets. Hence, despite the calculated (Method 2) superiority of OL(12) and its variants over OL(1C)mdr, it appears reasonable to conclude that OL(1C)mdr is the more active antisense ODN.

Example 3

As was done for the MDR1 gene transcripts in Example 2, the primary selection method was also used to design antisense ODNs to target selected regions within the MRP cDNA gene transcript, based on what is known in the literature about the functions of the various regions of the transcript (Cole et al., Science 258: 1650, 1992). Functional sites targeted included the 5'-cap site, the 5'-untranslated leader and the translational start site. In addition, other antisense ODNs were selected using the secondary selection method described above.

Relative antisense ODN activity among the various MRP antisense ODNs was determined in exactly the same manner as was described in Example 2 above for analysis of the MDR1 antisense ODNs, except that the MRP antisense ODNs were tested on the MRP-expressing, multidrug-resistant A427 human lung cancer cell line (Giard et al., J. Natl. Cancer Inst. 51: 1417, 1973). Table XVI summarizes the prototype MRP antisense ODNs tested in these studies, and shows their relative ranking in terms of in vitro drug-sensitizing activity. OL(8)MRP, which was selected using the secondary selection method, was found to be the most effective among the various MRP antisense ODNs tested.

Based on the results of our studies of variants of the most active antisense ODNs selected by the Secondary Selection Method, the latter selection method was modified to become the Tertiary Selection Method already described.

These data support the notion that the method of selecting "hotspots" for targeting antisense ODNs and for determining the best antisense ODNs for any given hotspot will yield highly active antisense ODNs for any gene of choice. These, in turn, can be used for the therapeutic purposes disclosed herein.

Evaluation of the Usefulness of the Aberrant Programming Model with the Novel Method Presented Herein for Selecting Highly Active Antisense ODNs for the Discovery of Antisense ODNs for Therapeutic Use in the Aberrant Programming Diseases The most important feature of the invention disclosed herein is the fact that it makes possible a straight-forward and comparatively simple approach to the discovery of novel therapeutics for the treatment of several major diseases that historically have been intractable with respect to the development of new therapies, such as, for example, cancer, atherosclerosis, AIDS and Alzheimer's Disease. Specifically, the Aberrant Programming disease model combined with the method disclosed herein for selecting highly active antisense ODNS makes the discovery of new therapeutic agents for these diseases a comparatively small scale screening process. In contrast, for example, conventional drug development for cancer has yielded no major new breakthrough drugs for more than a decade, despite the huge expense and the screening of hundreds of thousands of compounds.

To demonstrate a reduction of this invention to practice, the inventor decided to select a very small number of gene targets from those predicted by the Aberrant Programming model to be of therapeutic use and to design and test antisense ODNs directed to these targets on normal and cancer cells. The first gene target selected was junD (Hirai et al., EMBO J. 8: 1433, 1989; Ryder at al., Proc. Natl. Acad. Sci. USA 86: 1500, 1989). The reasons were the following: (1) junD is a TR involved in the control of cellular programming; (2) it is expressed by many types of both normal and malignant cells; and (3) the expression levels of junD and its physical state appear to be the same in both normal and malignant cells. Therefore, junD appears to be neither an oncogene nor an anti-oncogene in actual tumors seen in patients (certain junD mutants may, however, function as an oncogene in some experimental situations). Hence, if treatment of normal and malignant cells with antisense ODNs to junD leads to adverse effects on malignant but not on normal cells, then such data would constitute prima facia evidence in support of the Aberrant Programming model and its value for the development of novel therapeutics.

Example 4

Two junD antisense ODNs were tested in vitro: H(1)junD (SEQ ID NO. 5) and H(2)junD (SEQ ID NO. 6):

```
SEQ ID NO.5:   H(1)junD   GTCGGCGTGG TGGTGA

SEQ ID NO.6:   H(2)junD   GCTCGTCGGC GTGGTGGTGA
```

Control ODNs included those which had the same nucleotide base sequence but in the reverse order, as well as ODNs which were directed to irrelevant genes. These ODNs were designed using the criteria listed for the primary selection method, with the added restriction that (a) only hotspots capable of giving rise to antisense ODNs with no hairpins and no more than two contiguous base matches in a row for self-dimers were allowed; and (b) the melting temperature ($T_m$) had to be $\geq 40°$ C. for a 20-mer (corresponding to a negative kcal/mol value of $\leq -33.8$ kcal/mol or even more negative. Under these conditions, 26 acceptable hotspots were identified. The inventor decided to test initially antisense ODNs with binding affinities in the mid-range between the maximal value of $-33.8$ and the preferred values of $\leq -46.0$ kcal/mol. The hotspot with the 5'-terminal nucleotide of 515 was chosen. The corresponding 20-mer prototype antisense ODN [=H(2)junD] had a binding affinity of $-43.0$ kcal/mol. There were 11 acceptable hot spots in the junD sequence that would yield prototype antisense ODNs with this or even greater binding affinity. Based on subsequent work by the inventor, the selection criteria used for H(1)junD and H(2)junD ODN are expected to yield good but not necessarily exceptional antisense ODNs.

In the initial tests, the H(1)junD oligo or a control ODN were incubated with AML blast cells for seven days. The blast cells were freshly obtained from patients with AML and were cultured and evaluated for ODN effects as described by Bayever et al.(*Leukemia and Lymphoma* 12: 223-231, 1994). In brief, after the incubation with ODNs, the blast cells were then washed, and adjusted to $10^5$ cells per ml and continued in culture for several more days. Viable cell counts were performed every 2-3 days on suspension cultures and oligo-treated blast cells were plated in the "blast colony assay" to determine the effects of the ODNs on the leukemic stem cells. A representative example of the suspension culture data is shown in FIG. 3. H(1)junD is consistently found, as in the example shown, to have as great or a greater antileukemic effect than OL(1)p53. Similarly, H(1)junD has been found to have anticancer effects on solid tumors such as, for example, ovarian carcinoma.

To test the effects of the H(1)junD ODN on normal cells, normal human bone marrow cells were incubated with from 10 nM to 10 µM of the H(1)junD ODN for 7 days. The bone marrow cells were cultured and evaluated as described in Bayever et al. (op.cit.). In brief, viable cell counts were performed every two days following ODN treatment and then the cells were plated in mixed colony assays to determine what effects (if any) the ODNs would have on the proliferation and differentiation of various types of hematopoietic colony forming units. H(1)junD was not found to have any impact on normal cell growth, viability or differentiation.

When the H(1)junD and H(2)junD ODNs were tested on malignant cell lines, they were found to have less of a cytotoxic or anticancer growth-inhibitory effect than they had on freshly-obtained cancer specimens. However, the inventor discovered that these antisense ODNs could be used to dramatically sensitize various types of multidrug-resistant cancer cells to anti-cancer chemotherapeutic agents. Remarkably, these sensitizing effects were operative on cancer cells that have differing mechanisms for their multidrug resistance. Table XVII shows that H(1)junD or H(2)junD can be used to sensitize P-glycoprotein-expressing drug-resistant 8226/Dox cell to vincristine, while H(1)junD also can sensitize DU-145 prostate cancer cells that express MRP and not P-glycoprotein. These finding support the conclusion that suppressing the expression of junD, such as by treatment with antisense ODNs, can be used to reverse multidrug resistance resulting from any of a variety of mechanisms, including those that require expression of molecular transporters such as P-glycoprotein and MRP, and perhaps also the less-well characterized drug resistance mechanisms such as those producing resistance to cisplatin and related compounds. It has also been found that junD is up-regulated in cancer cells following treatment with the chemotherapeutic agent Ara-C (Kharbanda et al., Biochem. Pharm. 45: 2055, 1993). Hence, increased junD expression could be part of a cellular response mechanism that tends to block the toxic effects of chemotherapeutic agents on cancer cells.

In contrast to the effects on multidrug resistant cancer cell lines, the H(1)junD ODN had minimal sensitizing potential when used to treat drug-sensitive (parent) cancer cell lines (Table XVII). This difference in the responsiveness of the drug-resistant versus drug-sensitive cancer cells to H(1)junD is consistent with the prediction made by the Aberrant Programming model that the pattern of transcriptional regulator expression associated with different states of the Aberrant Programming diseases will vary in such a way that the effects of modulating these patterns with any particular modulator will produce somewhat different effects, depending on the specific character of the Aberrant Programming disease cells. Hence, the need for the type of novel diagnostic and prognostic testing disclosed herein. The junD antisense ODN data taken as a whole also illustrate that junD is involved in an abnormal combinatorial regulation system that maintains both (a) the viability of cancer cells, and (b) the drug resistance phenotype.

In conclusion, the Aberrant Programming model coupled with the antisense ODN 30 selection method disclosed, can readily be used to identify novel antisense ODNs with therapeutic potential for treating Aberrant Programming Diseases.

Selection of Hotspots and Prototype Antisense ODNs for Transcripts of Genes of Therapeutic Importance The tertiary selection method was applied to more than 200 genes and the resulting hotspots and prototype antisense ODNs are disclosed herein, in Tables XVIII and following. The selection of this large number of genes is based on the Aberrant Programming model and on the scientific literature concerning the probable/possible involvement of particular molecules or types of molecules in particular disease processes. The details of this extensive literature is readily available to anyone through computer searching of a variety of scientific and medical databases, using "keyword" searches. The list of genes for which hotspots have been identified herein should be expanded in the future. Certain genes (human) that are clearly of potentially great therapeutic importance have been identified, but either the gene sequences have not been made available or only partial sequences are available. The genes in the former category include telomerase which is implicated in the promotion of cancer, and several of the homeobox genes (including Hox A1, Hox A10, Hox B6, Hox C6, Hox 2.4, Hox 2.6 and Hox 5.4) which fall into both sequence categories. The homeobox genes are apt to be important for more than one of the Aberrant Programming diseases, and some are likely to be regulators of telomerase expression, for example. TR that are required for telomerase expression are potential targets for antisense therapeutics for the treatment of cancer. Once the MRP gene is completely sequenced, it is likely that the new sequence data will allow for more useful antisense ODNs to be designed for therapeutic inhibition of the gene. Other genes that are to be included in the list of possible therapeutic targets, for which sequences are not yet available, are mdm-2, LBP-1a,b,c and d, Rp-8, fos-B, ATBF1, hu-cut, maf, ERP, ELAM-1, ERM, AP-12, SAP-1, OxyR (human counterpart), HES-1, NM23-H1, LR1, and E2F1. Application of the tertiary selection method disclosed herein can and will be readily applied to these gene sequences as they become available. The resultant hotspots and the associated antisense ODNs will be utilized in the practice of this invention.

Treatment of Atherosclerosis Using Antisense ODNs directed to Transcriptional Reaulators or their Direct Modulators The present inventor, to the best of his knowledge, was the first to describe the c-myc gene (and perhaps the c-myb gene, as well) as being potentially useful gene targets for the treatment of atherosclerosis, since these gene targets encode transcriptional regulators known to be involved in the control of cellular programming. As previously reviewed herein, antisense ODNs directed to c-myc or c-myb have now been shown to have in vivo activity for inhibiting the proliferation of smooth muscle cells (SMC) following balloon angioplasty in atherosclerosis. In these publications, only a single c-myc antisense ODN, however, directed to the transcript of the human c-myc gene, has been tested. Analysis of this 15-mer c-myc antisense ODN by the criteria disclosed in the present invention indicate that this 15-mer is a very sub-optimal antisense ODN for the purpose of reducing c-myc expression. Specifically, it has four guanines in a row which may cause the formation of a "G-quartet" (as does the c-myb antisense ODN used to treat SMC) which is apt to inhibit the proliferation of some normal cell types independently of any direct effect on c-myc expression. In fact, it has been shown in the inventor's laboratory that an oligonucleotide comprising the reverse sequence of this 15-mer c-myc antisense ODN inhibited the proliferation of human lung cancer cell lines nearly as well as did the c-myc antisense ODN (unpublished data). Furthermore, the published 15-mer c-myc antisense ODN has a greater degree of self dimerization than is acceptable according to the criteria herein described in the present application, since it has six (6) contiguous base matches; similarly, it has a much lower binding affinity for its target than is desirable even in a 15-mer (only being –30.9 kcal/mol). The application of the tertiary selection method described herein will provide much improved c-myc antisense ODNs, as well as highly active c-myb antisense ODNs useful for modulating expression of the human c-myb gene, although the c-myb sequence has not proven to be a particularly good target.

It also is likely that the Reprogramming Test disclosed herein could be used to find genes that would be more suitable targets for antisense ODNs for the treatment of atherosclerosis/restenosis than are the c-myc and c-myb genes. This assumes, however, that the SMC involved in restenosis are atherosclerotic and not normal. If this is the case, then restenosis is just a particular form of atherosclerosis. Indeed, it could be argued that the published c-myc and c-myb antisense ODNs that have been used in the restenosis system work simply by inhibiting cell proliferation, and that many other antisense ODNs directed to other gene targets involved in the control of cell proliferation would work equally well. Such a broad effect based simply on inhibiting a cellular program (proliferation) from proceeding is very different from the cellular reprogramming effect which is the basis of the AP model approach. With respect to the strategy of simply inhibiting the proliferation of SMC following angioplasty, it would be preferable to use gene targets for antisense ODN inhibition that are more restricted to SMC than are c-myb or c-myc; such as, for example, NF-IL6. Antisense ODNs that can be effectively used to block cell proliferation have been disclosed herein.

According to the Aberrant Programming model, atherosclerotic SMC will express a different pattern of TR than is to be found in normal SMC. Therefore, finding the most appropriate TR target gene(s) requires a comparison of the effects of potential therapeutically-useful antisense ODNs on atherosclerotic SMC, along with normal cells (normal SMC, and normal bone marrow if possible). It would be preferable for the treatment of atherosclerosis generally to identify an antisense ODN capable of selectively inducing programmed cell death (or "apoptosis") in the atherosclerotic SMC while sparing normal cells. This could be achieved by the use of antisense ODNs of the type disclosed herein, used either alone or in combination with another augmentation agent also capable of modulating TR expression in atherosclerotic SMC, such as, for example, a growth factor. Miano et al.(Amer. J. Pathol. 142: 715, 1993) have observed that the TR c-fos, fos-B, fra-1, c-jun, jun-B and junD are expressed by SMC. Each of these, along with c-myc and c-myb, should be evaluated in the Reprogramming Test applied to atherosclerosis. The p53 gene is also expressed in atherosclerotic SMC and should be tested as a target gene along with genes regulated by p53, as well as those which, in turn, regulate p53 expression. These genes, along with the genes previously mentioned that are implicated in controlling changes in cellular programming in response to oxidative damage, should be evaluated as potential therapeutic targets for inhibition by antisense ODN. Atherosclerosis has been postulated by some to be an inflammatory disease linked to an abnormality in oxidation-mediated signals in the vasculature (Offermann et al., Heart Dis. Strokes 3: 52, 1994). Any other TR (or the direct modulators of the TR) involved in the control of cellular reprogramming that can be shown to be expressed in atherosclerotic SMC should also be evaluated in the Reprogramming Test. The preferred methods for screening for the expression of TR are provided herein. In addition, antisense ODNs directed to genes involved in programmed cell death (i.e., apoptosis) should be evaluated in the Reprogramming Test using atherosclerotic SMC. Genes such as E2F-1 and cyclin-A or cyclin-D1 that have been implicated in the expression of c-myc also should be given priority testing (Oswald et al., Oncogene 9: 2029, 1994). A listing of some of the in vitro and in vivo assays that should be of use for developing antisense ODNs for the treatment of AP diseases (including atherosclerosis) are provided in Table XIII.

The antisense oligonucleotide selected for practice of the invention may be any of the types described by Stein and Cohen, Cancer Research 48:2569-2668 (1988), and including without limitation, unmodified oligodeoxynucleotides, ethyl- or methylphosphonate modified oligodeoxynucleotides, phosphorothioate modified oligonucleotides, dithioates, as well as other oligonucleotide analogs, including those incorporating ribozyme structures, and oligoribonucleotides such as those described by Inove et al., Nucleic Acids Res. 15:6131 (1987); and Chimeric oligonucleotides that are composite RNA, DNA analogues (Inove, et al, *FEBS Lett.* 2115: 327 (1987). Oligonucleotides having a lipophilic backbone, for example, methylphosphonate analogs with ribozyme structures, may prove advantageous in certain circumstances; these molecules may have a longer half-life in vivo since the lipophilic structure may reduce the rate of renal clearance while the ribozyme structure promotes cleavage of the target RNA. Gerlach, Nature 334:585 (1988). Oligonucleotides with 2'-O-methylmodifiedribose sugars are also suitable for the practice of this invention. This ribose sugar modification can be used with a variety of backbone types such as phosphorothioates and may be limited to only some of the sugar residues such as those at the ends of the oligonucleotide.

The oligonucleotides may be formulated into pharmaceutical compositions and administered using a therapeutic regimen compatible with the particular formulation. As described further below, with the aid of present disclosure, those of skill in the chemotherapeutic arts should be able to derive suitable dosages and schedules of administration for any of a number of suitable compositions that contain the compounds. Thus, pharmaceutical compositions within the scope of the present invention include compositions where the active ingredient is contained in an effective amount to kill the cells of the cancer without causing unacceptable toxicity for the patient. However, a preferred dosage comprises that which is sufficient to achieve an effective blood concentration of between about 1 and about 5 micromolar. Although a preferred range has been described above, determination of the effective amounts for treatment of each type of tumor may be determined by those of skill in the art of chemotherapeutic administration.

In addition to the antisense oligonucleotide compounds, the pharmaceutical compositions of the invention may contain any of a number of suitable excipients and auxiliaries which facilitate processing of the active compounds into preparations that can be used pharmaceutically. Preferably, the preparations will be designed for parental administration. However, compositions designed for oral or rectal administration are also considered to fall within the scope of the present invention. Preferred compositions will comprise from about 0.1 to about 1% by weight of the active ingredients.

Suitable formulations for parental administration include aqueous solutions of the active compounds in water-soluble or water-dispersible form. Alternatively, suspensions of the active compounds may be administered in suitable lipophilic carriers. The formulations may contain substances which increase viscosity, for example, sodium carboxymethyl cellulose, sorbitol, and/or dextran. Optionally, the formulation may also contain stabilizers. Additionally, the compounds of the present invention may also be administered encapsulated in liposomes. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

While the present invention has been described in conjunction with a preferred embodiment and specific examples, the description is not meant to limit it. One of ordinary skill, with the aid of the present disclosure, may be able to effect various changes, substitutions of equivalents and other alterations to the methods and compositions set forth. Therefore, the protection granted by Letters Patent should not be limited except by the language of the claims as set forth below.

TABLE I

Analogy with Language
The following analogy with language illustrates the essential nature of the model of clinical cancer given in the patent application and the basic rationale for using antisense oligonucleotides directed against the indicated target or traitor genes as therapeutic agents. It should be clear that this is a novel, inventive and useful approach.

RULES:

| | Biology | Language Equivalent |
|---|---|---|
| 1. | The instructions for a particular pattern of gene expression (program) where key programs are differentiation, viability and proliferation | word |
| 2. | Transcriptional Regulators (or any of the other types of regulators listed as target or traitor genes) | letters |
| 3. | Programmed cell death | nonsense letter combination |
| 4. | Malignant cells have different program instructions than corresponding normal cells and normal cells in general | malignant cells express unique words |
| 5. | Normal cells at different stages of differentiation express different program instructions than other cell types | different normal cell types have their own vocabulary |
| 6. | All or nearly all the letters used by malignant cells are structurally normal and appear in normal cells | the alphabets of normal and malignant cells are essentially the same |
| 7. | As particular programs unfold, the pattern of regulators expressed changes | cells express different words at different program stages |

Note: The words used in the following examples have only a loose correlation to actual cellular behaviors or programs.

Hypothetical Example

| | Cell Type 1 (e.g. liver) | Cell Type 2 (e.g. kidney) |
|---|---|---|
| Normal | retard | stop |
| Low grade malignant | start | swarm |
| High grade malignant | spread | grow |

Comments—

I. ANALOGY WITH BASIC CLINICOPATHOLOGIC MECHANISMS a) "T" and "P" in normal cell type 2 but not in malignant type 1 could be considered analogous antioncogenes since they must be deleted for malignant progression. That is, for the word "stop" to be changed to the word "swarm". These deletions must occur along with the deletion of "o" and the addition of "w", "a", "r" and "m". The same letter "p", however, appears in the high grade malignant type 1 cell, while "t" appears in the low grade form. This fits the observations that antioncogenes are far from universally deleted in human cancers, that multiple genetic changes appear to be involved in carcinogenesis and that clinical cancers typically evolve phenotypically.

b) "m" and "w" could be considered analogous to "oncogenes" since they are required for "stop" evolving to "swarm" and they are not expressed in other normal adult cells. Alternatively, "m" and "w" could be normally only expressed at the embryonic-fetal stage of development.

c) "s" becomes expressed in the malignant forms of type 1 cells (ectopic expression) while it is normally expressed in type 2, but not type 1.

II. ANALOGY WITH ANTISENSE OLIGONUCLEOTIDE TREATMENT STRATEGY a) Inhibition of "t" expression will kill low grade type 1 calls but not normal cell types 1 and 2, because "start" becomes "sar" which is not a word, but "retard" and "stop" become "read" and "sop" respectively which are both words.

b) Blocking "m" but not "w" will kill malignant cell type 2 at the low grade phase since "swarm" minus "m" becomes "swar" which is not a word; but "swarm" minus "w" becomes "rams", a word.

d) Knocking out "a" will kill low grade 1 and 2 and high grade 1, but it also kills normal cell type 1. So antisense inhibition of "a" might be useful for purging bone marrow of malignant cell type 1 or 2 but not for systemic treatment.

TABLE I-continued

Analogy with Language
The following analogy with language illustrates the essential nature of the model of clinical cancer given in the patent application and the basic rationale for using antisense oligonucleotides directed against the indicated target or traitor genes as therapeutic agents. It should be clear that this is a novel, inventive and useful approach.

e) Deletion of "r" would not kill normal cell type 1 ("retard" becomes "date"), but it would kill three of the four malignant cell types. The exception being low grade 1 where "start" becomes "sat".
f) Removal of "e" kills normal and high grade type 1, so it would not be expected to be a good target for systemic therapy.
g) Of the remaining letters elimination of "d" or "g" will not result in the death of any of the cell types; removal of "s" will kill high grade 1, but none of the other cell types it appears in; blocking "o" will kill both malignant forms of type 2; and inhibition of "p" will kill high grade 1 but not normal type 2.

TABLE II

Human Transcriptional Regulators

| Members | Family | Where known to be expressed | Representative Reference | Possible Direct Modifications | Reference |
|---|---|---|---|---|---|
| p 53 | — | proliferating mature T and B lymphocytes, numerous types of cancer | Kern, et al., Sci. 252, 1708, 1991. | phosphorylation | Smith, et al., J. Exp. Med. 164, 751, 1986. |
| AZO | — | endothelial cells | Opipari, et al., J. Biol. Chem. 265, 14705, 1990. | — | — |
| AF-1 | — | liver | Metzger, et al., J. Bid. Chem 265, 9978, 1990. | — | — |
| AP-2 | — | cell lines | Comb and Goodman, Nucl. Acids Res. 18, 3975, 1990. | — | — |
| AP-4 | — | cell lines | Hu, et al., Genes and Dev. 4, 1741, 1990. | — | — |
| ATF1-8 | ATF | cell lines | Hoeffler, et al., Mole. Endocrine 5, 256, 1991. | — | — |
| C/EBP | — | liver | Friedman and Muknight, Genes and Dev. 4, 1410, 1990. | — | — |
| CHF.10 | — | cell lines | Pannuti, et al., Nucl. Acids Res. 16, 4227, 1988. | — | — |
| CHF.12 | — | cell lines | Pannuti, et al., Nucl. Acids Res. 16, 4227, 1988. | — | — |
| CRE-BP1 | — | fetal tissue, cell lines | Maekawa, et al., EMBO J. 8, 2023, 1989. | — | — |
| CREB | — | cell lines | Muchardt, et al., J. Virol. 64, 4296, 1990. | phosphorylation | Hoeffler, et al., Mol. Endo. 5, 256, 1991. |
| E12 | — | cell lines | Mosse, et al., Cell 56, 777, 1989. | — | — |
| E47 | — | cell lines | Mosse, et al., Cell 56, 777, 1989. | — | — |
| E2A | — | all blasts | Kamps, et al., 60, 535, 1990. | — | — |
| EBP1 | — | cell lines | Clark, et al., Genes Dev. 2, 991, 1988. | — | — |
| EGR 1-3 | EGR | cell lines, PMA induced mononuclear cells | Rangnekar, et al., Nucl. Acids Res. 18, 2749, 1990. | — | — |
| EGR 1,2 | ETS | cell lines | Watson, et al., PNAS 85, 7862, 1988. | — | — |
| ETS 1,2 | ETS | T lymphocytes, fetal liver, astrocytes | Bhat, et al., PNAS 87, 3723, 1990. | — | — |
| GLI-1-3 | GLI | embryonal carcinoma, myometrium, testis, placenta | Ruppert, et al., Mol. Cell. Biol. 8, 3104, 1988. | — | — |

TABLE II-continued

Human Transcriptional Regulators

| Members | Family | Where known to be expressed | Representative Reference | Possible Direct Modifications | Reference |
|---|---|---|---|---|---|
| HKR1-4 | HKR | testis, placenta, kidney, colon, lung, brain, embryomal carcinoma | Ruppert, et al., Hal. Cell. Biol. 8, 3104, 1988. | — | — |
| HOX 1.4, 2.1, 2.2, 2.3, 2.4, 2.5, 2.6, 2.7, 2.8, 2.9, 5.1, 5.2, 5.4, 6.1, 6.2, 7 | homeobox | cell lines, embryos | | | |
| HPFp1-9 | HPFp | placenta | Bellefroid, et al., DNA 8, 377, 1989. | — | — |
| H-plk | — | placenta | Kato, et al., Mol.. Cell. Biol. 10, 4401, 1990. | | |
| HS1 | — | lymphocytes | Kitamura, et al., Nucl. Acids Res. 17, 93167, 1989. | | |
| hXBP | — | lymphocytes | Liou, et al., Sci. 247, 1581, 1990. | | |
| $I_KB$ | — | placenta | Zabel and Baeuerle, Cell 61, 255, 1990. | | |
| ISGF1-3 | — | cell lines | Pine, et al., Mol. Cell. Biol. 10, 2448, 1990. | — | — |
| JUNB | JUN | cell lines | Nomura, et al., Nucle. Acids Res. 18, 3047, 1990. | — | — |
| C-JUN | JUN | cell lines | Nomura, et al., Nucle. Acids Res. 18, 3047, 1990. | — | — |
| JUN-D | JUN | cell lines | Nomura, et al., Nucle. Acids Res. 18, 3047, 1990. | | |
| K8 | homeobox | cell lines | Kongsuwan, et al., EMBOJ. 7, 2131, 1988. | — | — |
| lyl-l | — | cell lines | Mellentin, et al., Cell 58, 77, 1989. | | |
| MAX | — | cell lines | Blackwood and Eisenman, Sci. 251, 1211, 1991. | — | — |
| MBP-1 | — | cell lines | Baldwin, et al., Mol. Cell. Biol. 10, 1406, 1990. | — | — |
| A-myb | myb | cell lines | Normora, et al., Nucl. Acids Res. 16, 11075, 1988. | — | — |
| B-myb | myb | cell lines | Normora, et al., Nucl. Acids Res. 16, 11075, 1988. | | |
| C-myb | myb | cell lines, hematopoietic tissue | Normora, et al., Nucl. Acids Res. 16, 11075, 1988. | — | — |
| C-myc | myc | cell lines, hematopoietic tissue | Gazin, et al., EMBOJ. 3, 383, 1984. | | |
| L-myc | myc | placenta, lung cancer | Kaye, et al., Mol. Cell. Biol. 8, 186, 1988. | — | — |
| N-myc | myc | neuroblastoma | Slaman, et al., Sci. 232, 768, 1986. | — | — |
| myfS | — | muscle | Braun, et al., Nature 346, 663, 1990. | | |
| NF-E1,2 | NF-E | hematopoietic cells | Mignotte, et al., Nucl. Acids Res. 17, 37, 1989. | — | — |
| NFE6 | NF-E | hematopoietic cells | Colin, et al., J. Biol. Chem. 265, 16729, 1990. | — | — |
| NF-µE1 | — | lymphocytes | Sen and Saltimore, Cell 46, 705, 1986. | — | — |

TABLE II-continued

Human Transcriptional Regulators

| Members | Family | Where known to be expressed | Representative Reference | Possible Direct Modifications | Reference |
|---|---|---|---|---|---|
| NF-µE3 | — | lymphocytes | Sen and Saltimore, Cell 46, 705, 1986. | — | — |
| NFGMa | — | embryonic tissue, hematopoietic cells | Shannon, et al., Mol. Cell. Biol. 10, 2950, 1990. | — | — |
| NFGMb | — | hematopoietic cells | Shannon, et al., Mol. Cell. Biol. 10, 2950, 1990. | | |
| NF-IL6 | — | monocytes | Akira, et al., EMBO J. 9, 1897, 1990. | — | — |
| NP-$_K$B | — | lymphocytes, cell lines | Ruben, et al., Sci. 251, 1490, 1991. | — | — |
| NF-5 | — | lymphocytes | Kobr, et al., Mol. Cell. Biol. 10, 965, 1990. | — | — |
| 225 | — | cell lines, lymphocytes | Wright, et al., Sci. 248, 588, 1990. | — | — |
| 243 | — | lymphocytes | Bours, et al., Nature 348, 76, 1990. | — | — |
| Oct 1 | Oct | cell lines | Johnson, et al., Mol. Cell. Bid. 10, 1982, 1990. | — | — |
| Oct 2 | Oct | cell lines | Johnson, et al., Mol. Cell. Biol. 10, 1982, 1990. | — | — |
| Oct. 3 | Oct | embryonic | Scholer, et al.. EMBO J. 9, 2185, 1990 (murine) | — | — |
| Pit-1 | — | pituitary | Chen, et al., Nature 346, 583, 1990. | — | — |
| PL1 | homeobox | cell lines | Shen, et al., PNAS 86, 8536, 1989. | — | — |
| Pr1 | homeobox | cell lines | Kamps, et al., Cell 60, 547, 1990. | — | — |
| Rb | — | hematopoietic cells, retinal cells | Lee, et al., Sci. 235, 1394, 1987. | phosphorylation | Yen, et al., Exp. Cell. Res. 192, 289, 1991. |
| RF-y | — | cell lines | Reith, et al., Cell 53, 897, 1988. | — | — |
| RF-x | — | lymphocytes | Reith, et al., Genes Dev. 4, 1528, 1990. | — | — |
| Rhombotin | — | cell lines | McGuire, et al., Mol. Cell. Biol. 9, 2124, 1989. | — | — |
| SCL | — | fetal liver, hematopoietic cells, placenta | Beyley, et al., PNAS 86, 10128, 1989. | — | — |
| Sp-1 | — | cell lines | Pugh and Tjian, Cell 61, 1187, 1990. | — | — |
| SRF | — | cell lines | Norman, et al., Cell 55, 989, 1988. | — | — |
| Tal | — | cell lines | Chen, et al., EMBO J. 9, 415, 1990. | — | — |
| TCF-1 | — | lymphocytes | Van de Wetering, et al., EMBO J. 10, 123, 1991. | — | — |
| TFE3 | — | lymphocytes | Beckmann, et al., Genes Dev. 4, 167, 1990. | — | — |
| VAu | — | hematopoietic cells | Katzav, et al., EMBO J. 8, 2283, 1989. | — | — |
| cfos | fos | hematopoietic cells | Runkel, et al., Mol. Cell. Biol. 11, 1270, 1991. | phosphorylation | Barber and Verma, Mol. Cell. Biol. 7, 2201, 1987. |

TABLE II-continued

Human Transcriptional Regulators

| Members | Family | Where known to be expressed | Representative Reference | Possible Direct Modifications | Reference |
|---|---|---|---|---|---|
| fos-B | fos | cell lines | Mumberg et al. Genes Dev, 5, 1212, 1991 | — | — |
| fra-2 | fos | cell lines | Nishina et al., PNAS. 87, 3614 1990 (chicken) | — | — |
| glucocorticoid receptor | steroid receptor super family | lymphocytes and numerous other cell types | O'Malley, Mole Endocrin., 4, 363, 1990 | — | — |
| androgen receptor | steroid receptor super family | male reproductive organs, muscle | O'Malley, Mole Endocrin., 4, 363, 1990 | — | — |
| progesterone receptor | steroid receptor super family | female reproductive organs | O'Malley, Mole Endocrin., 4, 363, 1990 | — | — |
| estrogen receptor | steroid receptor super family | female reproductive organe | O'Malley, Mole Endocrin., 4, 363, 1990 | — | — |
| estrogen related receptors | steroid receptor super family | female reproductive organs | O'Malley, Mole Endocrin., 4, 363, 1990 | — | — |
| retinoic acid receptor | steroid receptor super family | hematopoietic cells, epithelial tissue | O'Malley, Mole Endocrin., 4, 363, 1990 | — | — |
| thyroid hormone receptor | steroid receptor super family | numerous tissues | O'Malley, Mole Endocrin., 4, 363, 1990 | — | — |
| vitamin D receptor | steroid receptor super family | hematopoietic and many other cell types | O'Malley, Mole Endocrin., 4, 363, 1990 | — | — |
| mineralocorticoid receptor | steroid receptor super family | kidney, colon, salivary glands | O'Malley, Mole Endocrin., 4, 363. 1990 | — | — |
| MZF-1 | Kruppel zinc finger like family | CML, placenta | Hromas, et al., J. Biol. Chem. 266, 14183, 1991 | — | — |
| HB9 | homeobox | hematopoietic, fetal | Deguchi and Kehrl, Blood 78, 323, 1991 | — | — |
| HB24 | homeobox | hematopoietic, fetal | Deguchi and Kebrl, Blood 78, 323, 1991 | — | — |
| vHNF1 | homeobox | liver | Bach, et al., Nucl. Acids Res. 19, 3553, 1991 | — | — |
| HOX11 | homeobox | liver, some T cell leukemias | Hatano, et al., Sci 253, 79, 1991 | — | — |
| PL2 | homeobox | cell lines | Lowney, et al., Nucl. Acids Res. 19, 3443, 1991 | — | — |
| rel | | cell lines | Brownell, et al., Mol. Cell Biol. 5, 2826, 1985 | — | — |
| HSF | | many cell types | Cunniff, et al., Mol. Cell Biol. 11, 3504, 1991 | — | — |
| NF-AB | | cell lines | Won and Baumann, Mol. Cell Biol. 11, 3001, 1991 | — | — |
| CCG1 | | cell lines | Sekiguchi, et al., Mol. Cell Biol. 11, 3317, 1991 | phosphorylated | Sekiguchi, et al., Mol. Cell. Biol., 11, 3317, 1991 |

TABLE II-continued

Human Transcriptional Regulators

| Members | Family | Where known to be expressed | Representative Reference | Possible Direct Modifications | Reference |
|---|---|---|---|---|---|
| rhom-2 | rhombotin | cell lines, embryonic tissue | Buehm, et al., PNAS 88, 4367, 1991 | | |
| rhom-3 | rhombotin | cell lines | Buehm, et al., PNAS 88, 4367, 1991 | | |
| GATA-3 | | T cells | Ho, et al., EMBO J. 10, 1187, 1991 | | |
| IP-1 | | cell lines | Auwerx and Sassone-Corsi, Cell 64, 983, 1991 | phosphorylated | Auwerx and Sassone-Corsi, Cell 64, 983, 1991 |

TABLE III

Scoring Features of Aberrant Programming Associated with Pathological Effects

| Disease | Cell Type | Representative Culture References | Pathological Features of Aberrant Programming | Pathologic Change Reference |
|---|---|---|---|---|
| Cancer | A) Hematopoietic | A-1) Eaves, et al., J. Tiss. Cult. Math. 13, 55, 1991. A-2) Messner, et al., Blood 70, 1425, 1987. A-3) Uckin and Heerema, Leuk. Lymph, 2, 1, 1990. A-4) Caligaris-Cappio, et al., Blood 77, 2688, 1991. A-5) Hoang and McCulloch, Blood 66, 748, 1985. | 1) inappropriate proliferation 2) ability to survive in inappropriate sites in body 3) inappropriately invasive | 1-3) Kissane (ed) Anderson's Pathology C. V. Mosby St. Louis, 9th ed. 1990. |
| | B) Solid Tissue | B-1) Moyer, J. Tiss. Cult. Meth. 8, 63, 1983. B-2) Moyer and Poste (eds.). Colon Cancer Cells, Academic Press, San Diego, CA 1990. (Dr. Moyers' culture system works for most primary human sarcomas and carcinomas) | | |
| Myelo-dysplasia | hematopoietic | a) Firken, et al., Br. J. Haemat. 75, 476, 1990. b) Aoki, et al., Amer. J. Hemat. 35, 6, 1990. c) Nagler. et al., Blood 76, 1299, 1990 | 1) impairment of blood cell differentiation as judged by standard clinical diagnostics 2) impaired colony formation by multi-potential progenitors 3) immune abnormalities including (a) deficits in CD4' lymphcytes and (b) decreased NK cells 4) apoptosis 4c) suppressed clonal expansion of myeloid progenitors from patients but not normals in presence of patient serum | 1-3) List, et al., J. Clin. Oncol. 1424, 1990. 4) Clark and Lampert, Leuk. Lymph. 2, 415, 1990. 4c) Donohue, et al., Nature 326, 200, 1982. |
| Myelo-proliferative Disorders | hematopoietic | a) Eaves, et al., J. Tiss. Cult. Meth. 13, 55, 1991. b) Messner, et al., Blood 70, 1425, 1987. c) Fauser and Messner, Blood 58, 1224, 1981. | inappropriate clonal proliferation of particular blood cell lineage | Adamson and Fi-alkon, Br. J. Haemat. 38, 299, 1978. |

TABLE III-continued

Scoring Features of Aberrant Programming Associated with Pathological Effects

| Disease | Cell Type | Representative Culture References | Pathological Features of Aberrant Programming | Pathologic Change Reference |
|---|---|---|---|---|
| ARC/AIDS | hematopoietic | Current protocols in immunology Coligan, et al. (eds.), John Wiley, Inc., N.Y. 1991 | 1) reduction in CD4' lymphocytes and an inversion of the CD4' to CD8' 2) reduction in CD16'CD8'CD3' cells 3) functional de-facts in lymphocytes including: (a) altered responses to certain antigens and mitogens; (b) defact in ability to under-go clonal expansion; (c) abnormalities in IL-2 receptor expression 4) functional defects in other blood cells (a) abnormal TNF production; (b) defective platelet production | 1) Fauci, Sci. 239, 617, 1988. 2) Mansour, et al., AIDS Res. Human Retro. 6, 1451, 1990. 3a) Pinching and Nye, Immunol. Today 11, 256, 1990. 3a) Allouche, et al., Clin. Exp. Imm. 81, 200, 1990. 3b) Pantaleo, et al., J. Immunol. 144, 1696, 1990 3c) Prince, et al., Clin. Exp. Immun. 67, 59, 1987. 4a) Otah, J. Int. Med. 228, 549, 1990. 4b) Zucker-Franklin and Cao, PNAS 86, 5595, 1989. |
| Atherosclerosis | smooth muscle | a) Orekhov, et al., Atherosclerosis 60, 101, 1986. b) Campbell and Campbell, Vascular Smooth Muscle in Culture, Vols. I and II, CRC Press, Boca Raton, FL, 1987. | Shift from contractile to synthetic phenotype. Features of latter include 1) proliferation 2) increased HLA-DR expression 3) loss of muscle proteins 4) growth factor production 5) synthesis of extracellular matrix 6) production of decay-accelarating factor 7) shift from media to intimal location | 1) Olsson (ed) Atherosclerosis: Biology and Clinical Science, Churchill Livingstone, NY 1987. 2) Jonasson, et al., J. Clin. Invest. 76, 125, 1985. 3) Glukhova, et al., PNAS 85, 9542, 1988. 4) Wilcox, et al., J. Clin. Invest. 82, 1134, 1988. 5) Mosse, et al., Lab. Invest. 53, 556, 1985. 6) Seifert and Hansson, J. Clin. Invest. 84, 597, 1989. 7) Betz, et al., J. Cell. Phys. 147, 385, 1991. |

TABLE IV

Representative Tissue Culture References for Primary Normal Human Tissue

| Tissue | Reference |
|---|---|
| Gasterointestinal (and a variety of other epithelial and mesenchymal cell types) | a) Moyer and Gendelman, J. Leuk. Biol. 49, 499, 1991. b) Moyer, J. Tiss. Cult. Meth. 13, 107, 1991. |
| bone marrow | Eaves, et al., J. Tissue Cult. Meth. 13, 55, 1991. |
| hematopoietic stem cells | a) Messner, et al., Blood, 70, 1425, 1987. b) Bernstein, et al., Blood 77, 2316, 1991. c) Caux, et al., Blood 75, 2292, 1990. |
| liver | Gomez-Lechan, et al., In Vitro Cell. Dev. Biol. 26, 67, 1990. |

TABLE V

Effect of p53 a.s. ODNs on in vitro growth of partially purified blasts from peripheral blood of patients with acute non-lymphocytic leukemia. Values represent triplicate cultures from seven separate experiments, a through g, including six different patients at either presentation or relapse. Peripheral blood leukemia blasts were isolated by Ficoll-Hypaque separation and sheep erythrocyte T-cell rosetting. Cells were plated at $5 \times 10^6$/ml in medium as described (*). Control cultures either contained no a.s. ODNs (control) or a.s. ODN to rev (HIV). A.s. ODNs were added 24 hours after plating. In A., aliquots were removed from culture on days 5, 10 and 15 and counted for Trypan blue exclusion. In B., cells were removed on day 10 washed to remove a.s. ODN. replated at $5 \times 10^6$/ml and counted 5 days later (day 15). nd = not done.

A.

| a.s. ODN | | a | | | b | | | c | | | d | |
|---|---|---|---|---|---|---|---|---|---|---|---|---|
| day | 5 | 10 | 15 | 5 | 10 | 15 | 5 | 10 | 15 | 5 | 10 | 15 |
| Control | 100 | 100 | 100 | 100 | 100 | 100 | 100 | 100 | nd | 100 | 100 | 100 |
| HIV | nd | nd | nd | 54 | 55 | 75 | 46 | 45 | nd | 100 | 79 | 89 |
| OL(1) | 88 | 4 | 1 | 0 | 0 | 0 | 22 | 4 | nd | 64 | 21 | 27 |
| A(1) | 51 | 74 | nd | 0 | 0 | 0 | 86 | 21 | nd | 64 | 43 | 29 |
| A(3) | 101 | 15 | 13 | 51 | 18 | 21 | 30 | 2 | nd | 41 | 24 | 24 |
| C(1) | 60 | 57 | 41 | nd | nd | nd | 49 | 15 | nd | 55 | 19 | 17 | percent viable cells of control

B.

percent of control

| a.s. ODN | | e Replated | | | f Replated | | | g Replated | |
|---|---|---|---|---|---|---|---|---|---|
| day | 5 | 10 | 15 | 5 | 10 | 15 | 5 | 10 | 15 |
| Control | 100 | 100 | 100 | 100 | 100 | 100 | 100 | 100 | 100 |
| HIV | 102 | 85 | 103 | 83 | 102 | 92 | 90 | 97 | 91 |
| OL(1) | 68 | 46 | 33 | 45 | 44 | 31 | 45 | 34 | 43 |
| A(1) | 77 | 46 | 37 | 53 | 44 | 71 | 59 | 75 | 64 |
| A(3) | 93 | 55 | 37 | 51 | 57 | 73 | 63 | 51 | 62 |
| C(1) | 72 | 49 | 41 | 53 | 59 | 37 | 66 | 63 | 77 |

* Buick, et al., Blood 54, 95, 1979.

TABLE VI

Effect of p53 a.s. ODNs on in vitro colony formation (CFU-L) of cells removed on either day 0 or 7 of the two of the cultures described in Table V (f and g). Values represent mean ± SD of triplicate cultures. Controls were as described in Table V. Cells were cultured according to B. Lange (*) at $1 \times 10^5$/ml. A fraction of the cells from day 7 colonies were washed and replated at $1 \times 10^5$/ml as described (*) in the absence of a.s. ODN. A colony was defined as >20 cells; day 7 control colonies varied from 70 to 240, day 14 colonies varied from 13 to 55. n.d. = not done.

| a.s. ODN | f replated | | g replated | |
|---|---|---|---|---|
| day | 7 | 14 | 7 | 14 |
| Control | 100 | 100 | 100 | 100 |
| HIV | 87 | 92 | 98 | 82 |
| OL(1) | 17 | 15 | 60 | 2 |
| A(1) | 28 | 138 | 79 | 262 |
| A(3) | 58 | 108 | 96 | 24 |
| C(1) | 23 | 8 | 81 | 4 |

* Lange, et al., Blood 70, 192, 1982.

TABLE VII

Effect of p53 a.s. ODN on in vitro growth of normal bone marrow. Values represent the cumulative mean ± SD of triplicate cultures from three separate experiments. Mononuclear cells were isolated by Ficoll-Hypaque separation. Cells were plated at $2 \times 10^6$/ml in medium as described (*) except for substituting horse for human serum. Control cultures either contained no a.s. ODN, or a.s. ODN to rev (HIV). A.s. ODNs were added 24 hours after plating. Aliquots were removed from culture on days 5 and 10, and counted for Trypan blue exclusion.

| | Viable cells $\times 10^5$ | |
|---|---|---|
| a.s. ODN | day 5 | 10 |
| Control | 12.7 ± 3.3 | 13.1 ± 2.5 |
| HIV | 11.8 ± 2.6 | 11.5 ± 2.2 |
| OL(1) | 12.1 ± 2.6 | 12.0 ± 1.8 |
| A(1) | 11.9 ± 2.1 | 12.2 ± 1.5 |
| A(3) | 12.1 ± 2.7 | 14.5 ± 1.4 |
| C(1) | 9.7 ± 2.0 | 10.9 ± 0.5 |

* Bayever. et al., Exp. Cell Rev. 179, 168, 1988.

TABLE VIII

Effect of p53 a.s. ODNs on in vitro colony formation of hematopoietic progenitors removed on day 7 from three of the normal bone marrow cultures described in Table VI. Values represent the cumulative mean ± SD of triplicate cultures. Controls were as described in Table V. Cells were cultured as described (*), except they were plated at $1 \times 10^6$/ml. A fraction of the cells front day 7 colonies were washed and replated at $5 \times 10^4$/ml for the CFU-Mix and BFU-E, or $1 \times 10^5$/ml for the CFU-GM as described (*). A colony was defined as >20 cells. All colonies were cultured in the absence of a.s. ODNs.

| a.s. ODN | CFU-Mix | BFU-E | CFU-GM |
|---|---|---|---|
| Control | 3.9 ± 4.5 | 4.4 ± 7.2 | 237.6 ± 100.1 |
| HIV | 1.1 ± 0.9 | 1.0 ± 1.0 | 329.1 ± 161.9 |
| OL(1) | 1.8 ± 1.8 | 15.8 ± 1.8 | 278.9 ± 117.9 |
| A(1) | 9.5 ± 6.7 | 11.6 ± 7.8 | 330.3 ± 123.8 |
| A(3) | 1.0 ± 1.0 | 1.3 ± 1.8 | 261.3 ± 90.2 |
| C(1) | 3.4 ± 4.1 | 1.0 ± 1.9 | 254.5 ± 94.9 |

* Messner, et al., Blood 70, 1425, 1987. Caux, et al., Blood 75, 2292, 1990.

TABLE IX

Method for non-human primate peripheral blood T-cell studies:

1. Heparinized blood was diluted by one third with HBSS, layered over Ficoll-Hypaque and centrifuged at 1600 r.p.m., for 40 minutes at 20° C.
2. Interface mononuclear cells were recovered and washed twice with HBSS, resuspended in RPMI 1640 with 10% FCS to $1 \times 10^6$/ml in the presence of PHA (10 µg/ml)
3. Cells were incubated at 37° C. in 5% $CO_2$ for 72 to 96 hours.
4. Cells were harvested, washed and replated at $5 \times 10^5$/ml in medium consisting of RPMI 1640 with 10% FCS and 10% IL-2.
5. After a 24 hour incubation the a.s. ODN was added to the culture at a 10 µM concentration.
6. At 2 to 3 day intervals an aliquot was removed and counted for Trypan blue exclusion.

BMC039-PHA-primed human T-cells Aug. 14, 1991 KMH
PHA stimulated → Day 4 wash + place in IL-2 =
"Day 0", "Day 1" add 10 µM oligo

| | Media | A(1) | Oh(1) | A(3) | C(1) | HIV-2 |
|---|---|---|---|---|---|---|
| Day 0 | $2 \times 10^6$/ml | $2 \times 10^6$/ml | $2 \times 10^6$/ml | $2 \times 10^6$/ml | $2 \times 10^6$/ml | $2 \times 10^6$/ml |
| Day 2 | $8 \times 10^5$ | 3.6 | 5 | 4.2 | 4.2 | 6.8 |
| | 8.2 | 4.4 | 5.2 | 5 | 5 | 7.4 |
| | 7.4 | 3.6 | 4 | 4 | 5.2 | 8.6 |
| | $7.9 \times 10^6$ | $3.9 \times 10^6$ | $4.7 \times 10^6$ | $4.4 \times 10^4$ | $4.8 \times 10^4$ | $7.6 \times 10^6$ |
| Day 4 | $11.2 \times 10^6$ | 7.2 | 5.6 | 4 | 9.2 | 10.6 |
| | 11.4 | 6.6 | 8 | 6 | 8.6 | 10.4 |
| | 10.6 | 8 | 6.2 | 7.2 | 7.8 | 10 |
| | $11.1 \times 10^6$ | $7.3 \times 10^6$ | $6.6 \times 10^6$ | $5.7 \times 10^6$ | $8.5 \times 10^6$ | $10.3 \times 10^6$ |
| Day 7 | $18.2 \times 10^6$ | 7 | 8.8 | 2.3 | 9.2 | 15.4 |
| | 19.6 | 7.4 | 6.6 | 10.4 | 2.0.8 | 14.2 |
| | 18.6 | 8.2 | 9.8 | 2.1.2 | 2.1.6 | 14.6 |
| | $18.9 \times 10^6$ | $7.5 \times 10^6$ | $8.4 \times 10^6$ | $11.5 \times 10^6$ | $10.5 \times 10^6$ | $14.7 \times 10^6$ |
| | $6.3 \times 10^6$ | 6.6 | 6.5 | 6.2. | 6.5 | 6.1 |
| Day 9 | $7.1 \times 10^6$ | 6.6 | 6.8 | 6.9 | 6.9 | 6.7 |

BMC028 - 2 samples of monkey PB Aug. 14, 1991 KMH
PHA prime → onto IL-2, then oligo

| | Media | A(1) | Oh(1) | A(3) | C(1) | HIV-2 |
|---|---|---|---|---|---|---|
| Day 0 | $2 \times 10^6$/ml | $2 \times 10^6$/ml | $2 \times 10^6$/ml | $2 \times 10^6$/ml | $2 \times 10^6$/ml | $2 \times 10^6$/ml |
| Day 1 | | 10 µM oligo | 10 µM oligo | 10 µM oligo | 10 µM oligo | 10 µM oligo |
| Day 4 | | | | | | |
| Primate A | $1.0 \times 10^6$ | 0.6 | 0.47 | 0.33 | 0.53 | 1.2 |
| | 1.13 | 0.47 | 0.47 | 0.27 | 0.4 | 1.0 |
| | $1.07 \times 10^6$ | $0.53 \times 10^5$ | $0.47 \times 10^5$ | $0.3 \times 10^5$ | $0.47 \times 10^5$ | $1.1 \times 10^6$ |
| Primate B | $1.93 \times 10^6$ | 1.67 | 0.67 | 0.73 | 0.53 | $1.6 \times 10^6$ |
| Day 6 | | | | | | |
| Primate A | $2.0 \times 10^6$ | 1.4 | 1.07 | 1.33 | 1.4 | 3.2 |
| | 2.93 | 1.2 | 1.33 | 1.07 | 1.2 | 2.67 |
| | $2.47 \times 10^6$ | $1.33 \times 10^6$ | $1.2 \times 10^6$ | $1.2 \times 10^6$ | $1.33 \times 10^6$ | $2.93 \times 10^6$ |
| Primate B | $2.2 \times 10^6$ | $1.2 \times 10^6$ | $0.7 \times 10^6$ | $1 \times 10^6$ | $0.8 \times 10^6$ | $2.3 \times 10^6$ |

TABLE IX-continued

Method for non-human primate peripheral blood T-cell studies:

Day 8
bacteria in A

| Primate B | $2.9 \times 10^6$ | $1 \times 10^6$ | $0.4 \times 10^6$ | $0.7 \times 10^6$ | $1.2 \times 10^6$ | $2.4 \times 10^6$ |

Day 10
bacteria emerging in B

On "Day 4" cells were removed, washed free of oligo and replated at $2 \times 10^6$/ml. Replated cells → single cells → * (Day 4 = $2 \times 10^6$/each)

TABLE X

Therapeutic Association of Gene Targets for which "Hotspots" and Prototype Antisense Oligonucleotides have been Disclosed Herein

| Gene Targets | Therapeutic Association |
|---|---|
| androgen receptor; AP-2,4; ATF genes; BSAP; C/EBP; C/EBPα,β; CDK genes; CHF.10,12; CREB α,β,δ,γ; CREBPa,1; CREM; CTF/NF1; cyclin genes; DB1; DP-1; E12; E2A; E2F-1,2,3,4; E2F-like protein; E4BP4; E4TF1; E47; Elk-1,2; Erg-1,2; Erk-1,2,3; ERM; EVX-1,2; estrogen receptor; c-fos; fra-1,2; gadd genes; Gata1,2,3,4; HB9; HB24; HLX-1; hox genes; h-plk; HS1; HTF4; Id-1,2,3; IRF-1,2; ISGF3; jun genes; Lyl-1; MAD genes; MADS; max genes; MSX1,2; MTF-1; Mxi-1; myb genes; myc genes; Mzf-1; Net; NF-ATc; NF-IL6β; NF-kβ; NF-kβ-2; Oct1,2,3,6; Oct-T1,2; OTF3, 3c; OZF; p53; p107; Rb; RBAP-1; RBP1,2; Ref-1; rel genes; SAP-1,2; Sp1,2,3,4; SCL; Spi-1,B; SRF; TR3,4; USF; WT-1; YY1. | AP Diseases, where potential targets are selected according to the AP model; reprogramming normal cells; suppressing virus expression and/or effects of virus on cells; suppressing and/or enhancing expression of particular host genes of clinical significance. |
| 5-alpha reductase | Cancer |
| β-amyloid precursor protein | Alzheimer's |
| Apolipoprotein B | Atherosclerosis; Chronic renal disease |
| Apolipoprotein epsilon 4 | Alzheimer's |
| CDK2, CDK5 | Alzheimer's |
| Cyclooxygenase-1,2 | Inflammation |
| Dopamine D-1,2 receptors | Schizophrenia |
| Epidermal growth factor receptor | Cancer |
| bFGF | Alzheimer's; Cancer; Rheumatoid Arthritis |
| FLT-1 | Cancer; Psoriasis; Rheumatoid Arthritis |
| FLT-3; FLT-4 | Cancer |
| FLT-3/FLK2(STk-1) | Inhibit proliferation of normal hematopoietic stem cells; e.g., to protect from chemotherapy |
| GADD genes | Destruction of cells subjected to DNA damaging agents; e.g., irradiation, or viral infection; and reverse of proliferation arrest of cells subjected to oxidative damage, such as, e.g., AIDS and ARC |
| hgp$_x$1 | Atherosclerosis; Cancer |
| HSP27 | Alzheimer's, Cancer |
| 5-HT$_2$ receptor | Schizophrenia |
| KDR/FLK-1 | Cancer; Rheumatoid Arthritis |
| MTS-1,2 | AIDS; ARC; Cancer; Expansion of proliferating normal cell populations |
| p34cdc2 | Cancer; Inhibiting normal cell growth |
| Pim-1 | Cancer |
| PKC genes | AIDS; Alzheimer's; ARC; Atherosclerosis; Cancer; Restenosis |
| Platelet-derived endothelial growth factor | Cancer; Rheumatoid Arthritis |
| Platelet-derived growth factor | Cancer; Atherosclerosis; Renal disease |
| Platelet-derived growth factor receptor | Cancer; Atherosclerosis; Renal disease |
| Prostaglandin endoperoxide synthase | Inflammation |
| Ref-1 | Cancer |
| TGFα,β | AIDS; Cancer; Inflammatory diseases; Psoriasis; Renal disease; Restenosis; Schizophrenia |
| TNFα | Multiple Sclerosis; Multiple-Systems Organ Failure Syndrome; Rheumatoid Arthritis; Toxic Shock Syndrome |
| TNFβ | Cancer; Inflammatory diseases; Multiple sclerosis |
| TRPM-2 | Alzheimer's |
| Vascular Endothelial Growth Factor | Cancer; Psoriasis; Rheumatoid arthritis |
| Waf-1 | AIDS; ARC; activate CDK genes; normal expansion of proliferating cell populations |

TABLE XI

Genes/Proteins (Other than Transcriptional Regulators) Implicated in the Regulation of Apoptosis

| | |
|---|---|
| Androgens | glucocorticoids |
| Apo-1 | growth factors |
| Bax a,b,g | Heat Shock Protein |
| bcl-2 | ICE |
| bcl-x | ICH-1L |
| bcl-xl | ICH-1S |
| bcl-xs | Mcl-1 |
| CD40 ligand | Neurotransmitters |
| cyclins | SGP-2 |
| DAD1 | TGF family |
| estrogen | TNF family |
| extracellular matrix | TRPM-2 |

TABLE XII

Medical Conditions/Diseases in Which Apoptosis is Implicated

AIDS
Alzheimer's disease
Amyotrophic lateral sclerosis
Atherosclerosis/restenosis
Cerebellar degeneration
Cancer
Glomerulonephritis, immune-mediated
Liver disease, toxin-induced
Multiple organ dysfunction syndrome
Multiple sclerosis
Myelodysplastic syndromes
Myocardial infarction
Parkinson's disease
Prostatic hyperplasia, benign
Reperfusion injury
Retinitis pigmentosa
Rheumatoid arthritis
Stroke
Systemic lupus erythematosis
Ulcerative colitis
Viral infections:

adenoviruses
cytomegaloviruses (CMV)
Epstein-Barr virus (EBV)
hepatitis C virus
herpesviruses
hemorrhagic fever viruses
human Immunodeficiency viruses (HIV)
influenza viruses
poxviruses
vaccinia viruses

TABLE XIII

Aberrant Programming Disease Models

AIDS (1) In vivo
        a) Yeung et al., J Exp Med 180: 1911, 1994
        b) Barnett et al., Science 266: 642, 1994
        c) Fultz, Clin Infect Dis 17 (Suppl 1): S230, 1993
        d) Livartowski et al., Cancer Detect Prevention 16: 341, 1992
    (2) In vitro
        a) Asmuth et al., AIDS 8: 205, 1994
        b) Truckenmiller et al., AIDS Res Hum Retroviruses 9: 445, 1993
        c) Fauci, Lymphokine Res 9: 527, 1990
        d) Lori et al., Science 266: 801, 1994

Alzheimer's Disease (1) Animal models reviewed:
        a) Myhrer, Neurosci Biobehavior Res 17: 195, 1993
        b) Anger, Neurotoxicology 12: 403, 1991
    (2) In vitro
        a) Adler et al., Proc Natl Acad Sci USA 88: 16, 1991
        b) Yoshikawa et al., Nature 359: 64, 1992
        c) Blass et al., J. Neurol Sci 121: 132, 1994
        d) Matsumoto, Biochim Biophys Acta 1225: 304, 1994
        e) Wainer et al., Adv Exp Med Biol 295: 415, 1991
        f) Altstiel and Sperber, Prog Neuropsychopharm Biol Psychiatry 15: 481, 1991
        g) Busciglio et al., J Neurochem 61: 1565, 1993

Atherosclerosis (1) In vivo
        a) Kappel et al., FASEB J 8: 583, 1994
        b) Fekete, Acta Vet Hung 41: 3, 1993
        c) Williams et al., Arch Pathol Lab Med 115: 784, 1991
    (2) In vitro
        a) Roth et al., Coron Artery Dis 4: 283: 1993
        b) Shrivastava et al., Methods Findings Exp Clin Pharmacol 15: 345, 1993

TABLE XIII-continued

Aberrant Programming Disease Models c) Graham et al., J Invest Surg 4: 487, 1991
        d) Couffinhal et al., Circ Res 74: 225, 1994
        e) Bjorkerud et al., Arterioscler Thromb 14: 644, 1994
        f) Babaev et al., Atherosclerosis 96: 189, 1992
        g) Pickering et al., J Amer Coll Cardiol 20: 1430, 1992
        h) Parkes et al., Amer J Pathol 138: 765, 1991

Cancer (1) In vivo
        a) Manzotti et al., Clin Exp Metastasis 11: 5, 1993
        b) Mule et al., J Immunother 12: 196, 1992
    (2) In vitro
        a) Hoffman, Cancer Cells 3: 86, 1991
        b) Moore and Minowada, Human Cell 5: 313, 1992
        c) Parchment et al., Int J Cell Cloning 10: 359, 1992
        d) Parkins and Steel, Brit J Cancer 62: 935, 1990
        e) Marshall et al., Stem Cells Dayt 11: 62, 1993
        f) Hanauske et al., Anticancer Drugs 3: 121, 1992
        g) Foulke et al., Cancer Res 50: 6264, 1990

Rheumatoid Arthritis (1) In vivo
        a) Plater-Zyberk et al., Clin Exp Immunol 98: 442, 1994
        b) Geiler et al, Arthritis Rheum 37: 1664, 1994
        c) Durie et al., Clin Immunol Immunopathol 73: 11, 1994
    (2) In vitro
        a) Partsch et al., Scand J Rheumatol 20: 98, 1991
        b) Johnstone et al., Autoimmunity 10: 35, 1991
        c) Sadouk et al., Clin Immunol Immunopathol 56: 37, 1990
        d) Goddard et al., Cytokine 2: 149, 1990

Schizophrenia (1) In vivo
        a) Okuyama et al., Life Sci 55: PL133, 1994
        b) Swerdlow et al., Arch Gen Psychiatry 51: 139, 1994
        c) Zhang et al., J Pharmacol Exp Ther 271: 1462, 1994
        d) Silvia et al., Mol Pharmacol 46: 51, 1994
        e) Zhou et al., J Pharmacol Exp Ther 268: 1015, 1994
        f) Zhang and Creese, Neurosci Lett 161: 223, 1993
        g) Weiss B et al., Neurosci 55: 607, 1993
    (2) In vitro
        a) Taylor et al., NIDA-Res-Monogr 133: 125, 1993
        b) Normal et al., J Med Chem 37: 2552, 1994

TABLE XIV

MDR-ODNs

| Oligo Name | 5'-end target site[1] | Oligo length (No. of bases) | Why the site was selected (Footnote #) | Relative Activity |
|---|---|---|---|---|
| OL(1)mdr | 1125[1] | 20 | 2 | +++ |
| OL(1A)mdr | 1122 | 20 | variant | ++ |
| OL(1B)mdr | 1123 | 22 | variant | ++++++ |
| OL(1C)mdr | 1125 | 25 | variant | +++++++ |
| OL(1Q)mdr | 1125 | 23 | variant | ++++++ |
| OL(1W)mdr | 1125 | 18 | variant | +++++ |
| OL(1Wa)mdr | 1123 | 18 | variant | ++++ |
| OL(1Wb)mdr | 1125 | 16 | variant | ++++ |
| OL(1Wc)mdr | 1121 | 18 | variant | ++++ |
| OL(1X)mdr | 1127 | 18 | variant | +++ |
| OL(2)mdr | 1688 | 20 | 2 | + |
| OL(3)mdr | 5996 | 20 | 2 | + |
| OL(5)mdr | 1000 | 20 | 2 | +++ |
| OL(6)mdr | 488 | 20 | 3 | + |
| OL(6A)mdr | 496 | 20 | variant | — |
| OL(7)mdr | 2199 | 20 | 3 | + |
| OL(8)mdr | 5722 | 20 | 3 | — |
| OL(9)mdr | 3881 | 20 | 2 | — |
| OL(10)mdr | 688 | 20 | 3 | +++ |
| OL(11)mdr | 851 | 20 | 3 | + |
| OL(12)mdr | 884 | 20 | 3 | +++ |

TABLE XIV-continued

MDR-ODNs

| Oligo Name | 5'-end target site[1] | Oligo length (No. of bases) | Why the site was selected (Footnote #) | Relative Activity |
|---|---|---|---|---|
| OL(12A)mdr | 881 | 22 | variant | +++++ |
| OL(12B)mdr | 885 | 18 | variant | +++ |
| OL(12C)mdr | 881 | 18 | variant | ++ |
| OL(13)mdr | 958 | 20 | 3 | — |
| OL(14)mdr | 5713 | 20 | 3 | — |
| OL(15)mdr | 941 | 20 | 3 | — |
| OL(16)mdr | 517 | 20 | 2 | + |
| SJ(1)mdr | 85 | 20 | splice junction | — |
| SJ(2)mdr | 673 | 20 | splice junction | ++ |
| SJ(6)mdr | 2559 | 20 | splice junction | + |
| SJ(18)mdr | 6074 | 20 | splice junction | + |
| SJ(30)mdr | 4867 | 20 | splice junction | — |
| SJ(33)mdr | 349 | 20 | splice junction | — |
| SJ(34)mdr | 540 | 20 | splice junction | +++ |
| SJ(34A)mdr | 542 | 18 | variant | +++++ |
| SJ(34B)mdr | 540 | 22 | variant | ++ |
| SJ(34C)mdr | 533 | 20 | variant | + |
| SJ(34D)mdr | 543 | 16 | variant | + |
| SJ(35)mdr | 1097 | 20 | splice junction | — |
| SJ(36)mdr | 6551 | 22 | splice junction | + |
| 3(1)mdr | 7051 | 20 | 3'-end | — |
| 5(1)mdr | 664 | 26 | 4, AUG start | ++ |
| 5(2)mdr | 640 | 28 | 4 | — |
| AP(1)mdr | 670 | 23 | 5; TR binding | + |
| AP(4)mdr | 636 | 22 | 5; TR binding | + |
| PA(1)mdr | — | 23 | reverse of AP(1) | + |
| TH(2)mdr | 2954 | 20 | published | + |
| CAP(2)mdr | 556 | 22 | cap site | + |
| LOW(3)mdr | 11 | 20 | low Tm | + |
| Cohen(1)mdr | 1130 | 15 | published | + |
| NF-kB(1)mdr | 296 | 22 | 5; TR binding | — |
| CAT(L)mdr | 432 | 20 | TR binding | — |
| Y-box-mdr | 464 | 22 | TR binding | — |

Reactivity: — = no effect; + = weak positive effect; +++++++ = very strong positive effect.
The relative reactivity indicated for each MDR-ODN summarizes results obtained with 8226/Dox4, 8226/Dox6 and CEM/Vlb10 multidrug-resistant cell lines.
1 The numbering for the 5'-end target site is based on Genbank entry HUMMDR1A01-through-HUMMDR1A26 (Chin et al., Mol. Cell. Biol. 9: 3808, 1989; Chen et al., J. Biol. Chem. 265: 506, 1990), considered as a continuous sequence with the nucleotide at the extreme 5'-end of the sequence being given the nucleotide base number 1.
2 The preferred prototype ODNs were selected using the secondary selection method, as described in the text of the Specification.
3 The "alternative" prototype ODNs are secondary sites that were selected manually.
4 These ODNs were designed to have sufficient binding affinity to the 5'-untranslated portion of the cDNA to potentially block the movement of the ribosome toward the AUG start site.
5 Binding sites of these oligos are within an enhancer for the MDR1 gene, the sequence of which is reported by Kohno et al., J. Biol. Chem. 265: 19690, 1990. (GenBank entry # HUMMDR1B/J05674).

TABLE XV

MRP-ODNs

| Oligo Name | 5'-end target site[1] | ODN length (No. of bases) | Why the site was selected (Footnote #) | Relative Activity |
|---|---|---|---|---|
| A(1)MRP | 194[1] | 20 | AUG start site | — |
| OL(2)MRP | 2114 | 20 | 3 | — |
| OL(3)MRP | 2848 | 20 | 2 | +++ |
| OL(4)MRP | 4154 | 20 | 3 | — |
| OL(5)MRP | 1210 | 20 | 3 | — |
| OL(6)MRP | 2516 | 20 | 3 | + |
| OL(7)MRP | 3155 | 20 | 3 | — |
| OL(8)MRP | 3539 | 20 | 2 | +++++ |
| OL(9)MRP | 3800 | 20 | 2 | + |
| OL(10)MRP | 4484 | 20 | 3 | ++ |
| OL(11)MRP | 4715 | 20 | 3 | — |
| OL(12)MRP | 89 | 20 | 3 | — |
| OL(13)MRP | 129 | 20 | 3 | — |
| OL(14)MRP | 220 | 20 | 3 | + |
| OL(15)MRP | 3312 | 20 | 3 | — |
| OL(16)MRP | 1580 | 20 | 3 | — |
| 3(2)MRP | 4836 | 20 | 3' end | — |
| 3(3)MRP | 4933 | 20 | 3' end | — |
| 5(2)MRP | 164 | 26 | 4 | +++ |
| 5(3)MRP | 24 | 26 | 4 | ++ |
| LOW(1)MRP | 351 | 20 | low $T_m$ | — |
| LOW(2)MRP | 714 | 20 | low $T_m$ | + |
| CAP(2)MRP | 1 | 19 | Cap site | + |

Reactivity: — = no effect; + = weak positive effect; +++++ = strong positive effect
1 The numbering for the 5'-end target site is based on Genbank entry HUM-MRPX/L05628 (Cole et al., Science 258: 1650, 1992) with the nucleotide at the extreme 5'-end of the sequence being given the nucleotide base number 1.
2 The preferred prototype ODNs were selected using the secondary selection method, as described in the text of the Specification
3 The "alternative" prototype ODNs are secondary sites that were selected manually.
4 These ODNs were designed to have sufficient binding affinity to the 5'-untranslated portion of the cDNA to potentially block the movement of the ribosome toward the AUG start site.

TABLE XVI

Sensitization of 8226/Dox4 myeloma cells to vincristine by the most active of the MDR-ODNs

| Oligonucleotide (Trivial Name) | Estimated Mean 3H-TdR Count (VCR dose = 0) (Method 1) | Estimated $IC_{50}$ (Method 1) | Fold Increase in Drug Sensitivity (Method 1) | Estimated $IC_{50}$ (Method 2) | Fold Increase In Drug Sensitivity (Method 2) |
|---|---|---|---|---|---|
| Media only | 159,500 | $1.28 \times 10^{-5}$M | — | $1.2 \times 10^{-5}$M | — |
| OL(1B)mdr | 120,800 | $1.79 \times 10^{-8}$M | 715 | $1.9 \times 10^{-9}$M | 6,315 |
| OL(1Q)mdr | 76,200 | $1.92 \times 10^{-8}$M | 667 | $<1 \times 10^{-10}$M | >120,000 |
| OL(12A)mdr | 159,500 | $2.97 \times 10^{-8}$M | 414 | $3.2 \times 10^{-8}$M | 375 |
| OL(12)mdr | 159,500 | $5.5 \times 10^{-8}$M | 233 | $6.0 \times 10^{-8}$M | 200 |
| SJ(34A)mdr | 100,300 | $6.81 \times 10^{-8}$M | 188 | $<1 \times 10^{-10}$M | >120,000 |

TABLE XVI-continued

Sensitization of 8226/Dox4 myeloma cells to vincristine by the most active of the MDR-ODNs

| Oligonucleotide (Trivial Name) | Estimated Mean 3H-TdR Count (VCR dose = 0) (Method 1) | Estimated $IC_{50}$ (Method 1) | Fold Increase in Drug Sensitivity (Method 1) | Estimated $IC_{50}$ (Method 2) | Fold Increase In Drug Sensitivity (Method 2) |
|---|---|---|---|---|---|
| OL(1C)mdr | 40,200 | $1.33 \times 10^{-7}$M | 97 | $<1 \times 10^{-10}$M | >120,000 |
| OL(12B)mdr | 159,500 | $7.39 \times 10^{-7}$M | 17 | $6.8 \times 10^{-7}$M | 18 |

METHOD 1: Based on parsimonious mathematical model fitting all the data for each MDR-ODN and the media control. According to this model, the log of the tritiated thymide (3H-TdR) uptake count is modelled as a linear function of powers of drug dose. Given the estimate of the parameters, one can compute the dose of drug required to produce an expected 3H-TdR uptake count equal to one-half that expected in the absence of drug (50% inhibitory concentration, or "IC50") but in the presence of the specific MDR-ODN used in the experimental groups. The fit with the experimental data is excellent ($R^2 > 0.99$). Hence, these values express the ability of a particular MDR-ODN to sensitize the multidrug resistant cancer cells to the drug independently of any effect the MDR-ODN used without drug might have on the cells.

METHOD 2: The data were plotted on graphs in which the X-axis was the log of the concentration of drug used in a given experiment group, while the Y-axis was "% Media Control" plotted on a linear scale, where $$\% \text{ media control} = \frac{\text{3H-TdR count for particular MDR-ODN and concentration of drug}}{\text{3H-TdR count for cells treated with same concentration of drug, but in absence of MDR-ODN}}$$

A line parallel to the X-axis is then drawn at the 50% media control value. A vertical line through the point at which this line intersects each of the (MDR-ODN + drug-dose) response curves indicates the drug IC50 value on the X-axis for that MDR-ODN.

TABLE XVII

Effects of junD, MDR- and MRP-ODNs on drug sensitivity of drug-resistant and drug-sensitive human tumor cell lines

| Oligonucleotide (Trivial Name) | Human Tumor Cell Line | Drug Activity ($IC_{50}$) | Fold increase in Drug Sensitivity |
|---|---|---|---|
| Media Control | 8226/Dox6 | $1.2 \times 10^{-5}$M | — |
| H(2)junD | " | $1.1 \times 10^{-8}$M | 1091 |
| H(1)junD | " | $2.4 \times 10^{-8}$M | 500 |
| OL(1C)mdr | " | $6.3 \times 10^{-8}$M | 190 |
| SJ(34A)mdr | " | $2.3 \times 10^{-7}$M | 52 |
| OL(12A)mdr | " | $3.1 \times 10^{-7}$M | 39 |
| reverse-H(1)junD | " | $1.9 \times 10^{-5}$M | 0 |
| Media Control | 8226/sensitive | $2.0 \times 10^{-9}$M | — |
| H(1)junD | " | $7.2 \times 10^{-10}$M | 3 |
| OL(1C)mdr | " | $2.3 \times 10^{-9}$M | 0 |
| SJ(34A)mdr | " | $1.9 \times 10^{-9}$M | 0 |
| OL(8)MRP | " | $1.5 \times 10^{-9}$M | 0 |
| Media Control | DU-145 | $3.5 \times 10^{-9}$M | — |
| H(1)junD | " | $1.8 \times 10^{-8}$M | 19 |
| OL(1C)mdr | " | $3.6 \times 10^{-9}$M | 0 |
| SJ(34A)mdr | " | $3.5 \times 10^{-9}$M | 0 |
| OL(8)MRP | " | $2.1 \times 10^{-8}$M | 17 |

8226/Sensitive = drug-sensitive parent cell line, human myeloma tumor (RPMI 8226; ATCC #CCL-155)
8226/Dox6 = multidrug-resistant variant of 8226/S, over-expressing MDR1, and resistant in vitro to $6 \times 10^{-8}$M doxorubicin
DU-145 = multidrug-resistant human prostate cancer cell line, over-expressing the MRP gene Lengthy table referenced here

US07517644-20090414-T00001

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US07517644B1). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07517644B1). An electronic copy of the "Sequence Listing" will also be available from the USPTO upon request and payment of the fee set forth in 37 CFR 1.19(b)(3).

What is claimed is:

1. A method for rational discovery of antisense oligonucleotides useful as therapeutics for the treatment of an Aberrant Programming Disease wherein said Aberrant Programming Disease is cancer, comprising the steps of (i) selecting one or more transcriptional regulator gene targets implicated in the regulation of cellular programming, said transcriptional regulator targets are not oncogenes and are expressed by cancer cells to be reprogrammed; (ii) selecting one or more prototype antisense oligonucleotides(s) to target transcripts of the selected non-oncogene transcriptional regulators, where said prototype antisense oligonucleotide(s) is selected from the group of oligonucleotides comprising SEQ ID NO: 1 through SEQ ID NO: 3626; (iii) evaluating said prototype antisense oligonucleotide(s) in a Reprogramming Test, alone and then in combination with an augmentation agent, for capacity to therapeutically reprogram the Aberrant Programmed disease cells while not adversely reprogramming normal cells, said augmentation agent being capable of altering the pattern of transcriptional regulator expression in the Aberrant Programmed disease cells; (iv) selecting sequence- and length-variants of prototype oligonucleotides scored in the Reprogramming Test to exhibit capacity to reprogram Aberrant Programming cells; (v) evaluating said variants for efficacy in the Reprogramming Test, either alone or in combination with the appropriate augmentation agent; (vi) selecting the most active of the evaluated antisense oligonucleotides, or antisense oligonucleotide/augmentation agent combination, and testing the same in vivo for efficacy.

2. The method of claim 1, wherein said augmentation agent is selected from the group consisting of a cytokine, a cancer chemotherapeutic agent, and a generator of free-radicals.

3. A method for discovering oligonucleotide therapeutics for the treatment of diseases dependent on an inappropriate expression or suppression of the physiological death program, apoptosis, that involves the steps of (i) selecting a target gene known to be directly involved in the regulation of apoptosis by determining if the gene is expressed by said disease and as appropriate where said gene target is thought to promote or inhibit apoptosis; (ii) contacting normal and disease cells with antisense oligonucleotides designed by a Tertiary Selection Method to identify those that are most therapeutically active on the diseased cells; (iii) testing variants of these most active antisense oligonucleotides for increased efficacy in treating the diseased cells; and (iv) testing the most active oligonucleotides for toxicity and in vivo efficacy.

4. A method for identifying oligonucleotide therapeutics for treatment of aberrant programming diseases or medical disorders caused by dysregulated apoptosis, said method comprising:
   a) selecting a target gene sequence which regulates cellular programming;
   b) determining that said target gene is present and expressed in aberrant programmed diseased cells;
   c) selecting at least one antisense molecule consisting essentially of a sequence selected from the group of prototype oligonucleotide sequences set forth in Table 19;
   d) incubating the aberrantly programmed diseased cells in the presence and absence of said at least one antisense molecule;
   e) identifying those antisense molecule(s) which affect apoptosis of said diseased cells relative to control untreated diseased cells;
   f) contacting normal cells with the antisense molecule(s) identified in step e) and
   g) identifying those antisense molecules which differentially affect apoptosis in aberrantly programmed cells versus normal cells.

5. A method as claimed in claim 4, wherein said medical disorder is selected from the group of disorders selected from the group consisting of cancer and prostatic hyperplasia.

6. A method as claimed in claim 4, wherein said disorder is Alzheimer's disease.

7. A method as claimed in claim 4, wherein said disease is cancer.

8. A method as claimed in claim 4, wherein viability of said cells is assessed by metabolic labeling.

9. The method as claimed in claim 4, further comprising the step of assessing the oligonucleotide therapeutic so identified for efficacy and toxicity in an in vivo animal model.

10. A method as claimed in claim 4, wherein said antisense molecule of step g) inhibits apoptosis.

11. A method as claimed in claim 4, wherein said antisense molecule of step g) promotes apoptosis.

12. A method for rational discovery of antisense oligonucleotides useful as therapeutics for the treatment of an Aberrant Programming Disease wherein said Aberrant Programming Disease is cancer, comprising the steps of (i) selecting one or more gene targets implicated in cancer; (ii) selecting one or more prototype antisense oligonucleotides(s) to target cancer related transcripts, where said prototype antisense oligonucleotide(s) is selected from the group of oligonucleotides comprising SEQ ID NO: 1 through SEQ ID NO: 3626; (iii) evaluating said prototype antisense oligonucleotide(s) for efficacy in inhibition of cancer cell growth while not affecting the growth of normal cells, alone and then in combination with an augmentation agent, (iv) selecting sequence- and length-variants of prototype oligonucleotides which inhibit the growth of cancer cells while not affecting normal cells, (v) evaluating said variants for efficacy in the cancer cell specific growth inhibition, either alone or in combination with the appropriate augmentation agent; (vi) selecting the most active of the evaluated antisense oligonucleotides, or antisense oligonucleotide/augmentation agent combination and testing the same in vivo for efficacy.

13. The method as claimed in claim 12, wherein said prototype oligonucleotides are selected from the group consisting of 5-alpha reductase (SEQ ID NOS: 7-45), epidermal growth factor receptor (SEQ ID NOS: 941-950), FLT-1 (SEQ ID NOS: 1146-1161) FLT-4 (SEQ ID NOS: 1162-1197), hgpX1 (SEQ ID: 1423-1468), KDR/FLK-1 (SEQ ID NOS: 2105-2125), MTS-1 (SEQ ID NOS: 2322-2340), MTS-2 (SEQ ID NOS: 2341-2361), p34cdc2 (SEQ ID NOS:2782-2805), Pim-1 (SEQ ID NOS: 2878-2909), PKC (SEQ ID NOS:2910-3045), Platelet derived endothelial growth factor (SEQ ID NOS:2816-2839), Platelet derived growth factor receptor (SEQ ID NOS:2840-2862), ref-1 (SEQ ID NOS: 3121-3142), TGFβ (SEQ ID NOS:3291-3314), and vascular endothelial growth factor (SEQ ID NOS: 3509-3563).

14. The method as claimed in claim 1, wherein said antisense oligonucleotides hybridize to a transcriptional regulator selected from the group consisting of: ets-1; ets-2; c-jun; jun-B; jun-D; id-1; id-2; id-3; Gadd-45; hox 1.3; mcl-1; nf kappa B; waf-1; Rb; p107; nf-atc; p53; and Rb-2.

15. The method as claimed in claim 3, wherein said antisense oligonucleotides are selected from the group consisting of those which hybridize to Bax-alpha (SEQ ID NOS: 239-253), BCL-X (SEQ ID NOS: 254-263, BCL-XL (SEQ ID NOS:264-278), BCL2-alpha (SEQ ID NOS:279-312, BCL-2 beta (SEQ ID NOS:313-317), Cyclin (SEQ ID NOS: 653-699), DAD-1 (SEQ ID NOS: 700-738), FAS/APO-1 (SEQ ID NOS: 1139-1145), ICE (SEQ ID NOS: 1919-1933), ICH-1L (SEQ ID NOS: 1934-1950), ICH-1S (SEQ ID NOS: 1951-1964), MCL-1 (SEQ ID NOS: 2231-2264), SGP2 (SEQ ID NOS: 3175-3197).

16. The method as claimed in claim 4, wherein said antisense oligonucleotides are selected from the group consisting of those which hybridize to Bax-alpha (SEQ ID NOS: 239-253), BCL-X (SEQ ID NOS: 254-263), BCL-XL (SEQ ID NOS:264-278), BCL2-alpha (SEQ ID NOS:279-312, BCL-2 beta (SEQ ID NOS:313-317), Cyclin (SEQ ID NOS: 653-699), DAD-1 (SEQ ID NOS: 700-738), FAS/APO-1 (SEQ ID NOS: 1139-1145), ICE (SEQ ID NOS: 1919-1933), ICH-1L (SEQ ID NOS: 1934-1950), ICH-1S (SEQ ID NOS: 1951-1964), MCL-1 (SEQ ID NOS: 2231-2264), SGP2 (SEQ ID NOS: 3175-3197).

17. A method as claimed in claim 12, wherein said gene target implicated in the development of cancer is selected from the group consisting of BCL-XL, cdk-2, cdk-4 inhibitor, erk, BCL2-alpha, BCL-2 beta, and TNF-alpha.

* * * * *